US012760123B2

(12) United States Patent
Cook et al.

(10) Patent No.: US 12,760,123 B2
(45) Date of Patent: *Oct. 13, 2026

(54) BISPECIFIC ANTIBODIES BINDING HVEM AND CD9

(71) Applicant: UCB BIOPHARMA SRL, Brussels (BE)

(72) Inventors: David Alan Cook, Slough (GB); Helen Margaret Finney, Slough (GB); Stephen Edward Rapecki, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 1049 days.

This patent is subject to a terminal disclaimer.

(21) Appl. No.: 17/929,028

(22) PCT Filed: Feb. 13, 2020

(86) PCT No.: PCT/EP2020/053773

§ 371 (c)(1),
(2) Date: Aug. 10, 2022

(87) PCT Pub. No.: WO2021/160266

PCT Pub. Date: Aug. 19, 2021

(65) Prior Publication Data

US 2023/0192900 A1 Jun. 22, 2023

(51) Int. Cl.
*C07K 16/46* (2006.01)

(52) U.S. Cl.
CPC ........ *C07K 16/468* (2013.01); *C07K 2317/24* (2013.01); *C07K 2317/31* (2013.01); *C07K 2317/565* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,858,358 | A | 1/1999 | June et al. |
| 7,288,638 | B2 | 10/2007 | Jure-Kunkel et al. |
| 8,197,809 | B2 | 6/2012 | Park et al. |
| 2011/0293579 | A1 | 12/2011 | Nielsen et al. |
| 2017/0081404 | A1 | 3/2017 | Finney et al. |
| 2017/0355755 | A1 | 12/2017 | Chen |

(Continued)

FOREIGN PATENT DOCUMENTS

| | | | |
|---|---|---|---|
| EP | 0336379 | B1 | 2/1996 |
| EP | 1532984 | A1 | 5/2005 |

(Continued)

OTHER PUBLICATIONS

Touzet et al. (2019) CD9 in acute myeloid leukemia: Prognostic role and usefulness to target leukemic stem cells. Cancer Medicine. 8:1279-1288. DOI: 10.1002/cam4.2007 (Year: 2019).*

(Continued)

*Primary Examiner* — Amy E Juedes
*Assistant Examiner* — Hilary Ann Petrash
(74) *Attorney, Agent, or Firm* — MEDLER FERRO WOODHOUSE & MILLS PLLC

(57) ABSTRACT

The present invention relates to multispecific antibodies against a novel targets' combination of HVEM and CD9, and their use in the treatment of cancer and infectious diseases.

12 Claims, 16 Drawing Sheets

Specification includes a Sequence Listing.

(56) References Cited

U.S. PATENT DOCUMENTS

| | | | | |
|---|---|---|---|---|
| 2019/0330366 | A1* | 10/2019 | Eckelman | C07K 16/2827 |
| 2021/0355219 | A1* | 11/2021 | Lin | A61P 35/00 |

FOREIGN PATENT DOCUMENTS

| | | | |
|---|---|---|---|
| WO | 98/25967 | A1 | 6/1998 |
| WO | 2005/035584 | A1 | 4/2005 |
| WO | 2009/023955 | A1 | 2/2009 |
| WO | 2014/028560 | A2 | 2/2014 |
| WO | 2017/072183 | A1 | 5/2017 |
| WO | 2017/119811 | A1 | 7/2017 |
| WO | 2017/174331 | A1 | 10/2017 |
| WO | 2018/114748 | A1 | 6/2018 |
| WO | 2018/114754 | A1 | 6/2018 |
| WO | 2018/187215 | A1 | 10/2018 |
| WO | 2019/179391 | A1 | 9/2019 |
| WO | 2021/160265 | A1 | 8/2021 |
| WO | 2021/160266 | A1 | 8/2021 |
| WO | 2021/160267 | A1 | 8/2021 |
| WO | 2021/160268 | A1 | 8/2021 |
| WO | 2021/160269 | A1 | 8/2021 |

OTHER PUBLICATIONS

Lichtenegger et al. (2013) Coinhibitory expression profiling of AML blasts identifies HVEM as a prognostic marker in AML. Blood vol. 122, Iss 21, doi: 10.1182/blood.V122.21.1359.1359 (Year: 2013).*

Park et al. (2012) Expression of anti-HVEM single-chain antibody on tumor cells induces tumor specific immunity with long term memory. Cancer Immunol Immunother 61:203-214, doi: 10.1007/s00262-011-1101-8 (Year: 2012).*

Wang et al. 2012. A herpes simplex virus 2 glycoprotein D mutant generated by bacterial artificial chromosome mutagenesis is severely impaired for infecting neuronal cells and infects only vero cells expressing exogenous HVEM. Journal of Virology. vol 86, No. 23, pp. 12891-12902, DOI: 10.1128/JVI.010 (Year: 2012).*

Harrop et al. (1998) Herpesvirus entry mediator ligand (HVEM-L), a novel ligand for HVEM/TR2, stimulates proliferation of T cells and inhibits HT29 cell growth. J. Biolog. Chemistry, vol. 273, No. 42, pp. 27548-27556 (Year: 1998).*

International Search Report, International Application No. PCT/EP2020/053773, Mailing Date: Oct. 16, 2020.

Akbar et al., "The Effect of a Chimeric Mouse-Human CD7 Antibody on Human T, Natural Killer, and Lymphokine-Activated Killer Cell Activity In Vitro," Transplantation 52(2):325-330 (1991).

Dahlén et al., "Bispecific antibodies in cancer immunotherapy," Therapeutic Advances in Vaccines and Immunotherapy 61(1):3-17 (2018).

Finney et al., "Activation of Resting Human Primary T cells with Chimeric Receptors: Costimulation from CD28, Inducible Costimulator, CD134, and CD137 in Series with Signals from the TCR Zeta Chain," The Journal of Immunology 172:104-113 (2004).

Flavell et al., "Characteristics and performance of a bispecific F (ab'y)2 antibody for delivering saporin to a CD7+ human acute T-cell leukaemia cell line," Br. J. Cancer 64:274-280 (1991).

Hoseini et al., "Acute myeloid leukemia targets for bispecific antibodies," Blood Cancer Journal 7(2):e522, 12 pages (2017).

Huan et al., "Overexpression of CD9 correlates with tumor stage and lymph node metastasis in esophageal squamous cell carcinoma," Int J Clin Exp Pathol 8(3):3054-3061 (2015).

Hwang et al., "Upregulation of CD9 in ovarian cancer is related to the induction of TNF-alpha gene expression and constitutive NF-kB activation," Carcinogenesis 33(1):77-83 (2012).

Ikeyama et al., "Suppression of Cell Motility and Metastasis by Transfection with Human Motility-related Protein (MRP-1/CD9) DNA," J. Exp. Med. 177:1231-1237 (1993).

Kischel et al., "Overexpression of CD9 in Human Breast Cancer Cells Promotes the Development of Bone Metastases," Anticancer Research 32:5211-5220 (2012).

Kontermann et al., "Bispecific antibodies," Drug Discovery Today 20(7):838-847 (2015).

Lazarovits et al., "CD7 is associated with CD3 and CD45 on human T cells," The Journal of Immunology 153(9):3956-3966 (1994).

Liu et al., "Tumor-antigen expression-dependent activation of the CD137 costimulatory pathway by bispecific DART proteins," Retrieved from the Internet: URL:http://cancerres.aacrjournals.org/cont ent/77/13_Supplement/3642 (Jul. 1, 2017).

Makkouk et al., "Rationale for anti-CD137 cancer immunotherapy," European Journal of Cancer 54(1):112-119 (2016).

Masellis-Smith et al., "CD9-regulated adhesion. Anti-CD9 monoclonal antibody induce pre-B cell adhesion to bone marrow fibroblasts through de novo recognition of fibronectin.," The Journal of Immunology 152:2768-2777 (1994).

Murayama et al., "Novel CD9-targeted therapies in gastric cancer," World Journal of Gastroenterology 21(11):3206-3213 (2015).

Nakamoto et al., "A novel therapeutic strategy with anti-CD9 antibody in gastric cancers," J Gastroenterol 44:889-896 (2009).

Park et al., "Anti-CD9 monoclonal antibody-stimulated invasion of endometrial cancer cell lines in vitro: possible Inhibitory effect of CD9 in endometrial cancer invasion," Molecular Human Reproduction 6(8):719-725 (2000).

Rabinowich et al., "Expression and function of CD7 molecule on human natural killer cells," The Journal of Immunology 152(2):517-526 (1994).

Rappa et al., "Tetraspanin CD9 determines invasiveness and tumorigenicity of human breast cancer cells," Oncotarget 6(10):7970-7991 (2015).

Reyes et al., "Tetraspanin CD9: A Key Regulator of Cell Adhesion in the Immune System," Frontiers in Immunology 9 (863):1-9 (2018).

Sanchéz-Paulete et al., "Cancer Immunotherapy with Immunomodulatory Anti-CD137 and Anti-PD-1 Monoclonal Antibodies Requires BATF3-Dependent Dendritic Cells," Cancer Discovery 71:71-99 (2015).

Segal et al., "Results from an Integrated Safety Analysis of Urelumab, an Agonist Anti-CD137 Monoclonal Antibody," Clinical Cancer Research 23(8):1929-1936 (2017).

Segal et al., "Phase I Study of Single-Agent Utomilumab (PF-05082566), a 4-1BB/CD137 Agonist, in Patients with Advanced Cancer," Clinical Cancer Research 24(8):1816-1823 (2018).

Sempowski et al., "Structure and Function of the CD7 Molecule," Critical Reviews in Immunology 19:331-348 (1999).

Tai et al., "A Role for CD9 Molecules in T Cell Activation," J. Exp. Med. 184(2):753-758 (1996).

Tai et al., "CD9-Mediated Costimulation of TCR-Triggered Naïve T Cells Leads to Activation Followed by Apoptosis," The Journal of Immunology 159(8):3799-3807 (1997).

Toyo-Oka et al., "Synergy between CD28 and CD9 costimulation for naïve T-cell activation," Immunology Letters 58(1):19-23 (1997).

International Search Report & Written Opinion, International Application No. PCT/EP2020/053771, Mailing Date: Oct. 16, 2020, 14 pages.

International Search Report & Written Opinion, International Application No. PCT/EP2020/053777, Mailing Date: Oct. 20, 2020, 16 pages.

International Search Report & Written Opinion, International Application No. PCT/EP2020/053780, Mailing Date: Nov. 23, 2020, 19 pages.

International Search Report & Written Opinion, International Application No. PCT/EP2020/053788, Mailing Date: Oct. 9, 2020, 12 pages.

Non-final Office Action issued in U.S. Appl. No. 17/929,031 mailed Dec. 16, 2025.

* cited by examiner

SEQUENCE LISTING

```
<160> NUMBER OF SEQ ID NOS: 22

<210> SEQ ID NO 1
<211> LENGTH: 283
<212> TYPE: PRT
<213> ORGANISM: homo sapiens

<400> SEQUENCE: 1

Met Glu Pro Pro Gly Asp Trp Gly Pro Pro Pro Trp Arg Ser Thr Pro
1               5                   10                  15

Lys Thr Asp Val Leu Arg Leu Val Leu Tyr Leu Thr Phe Leu Gly Ala
            20                  25                  30

Pro Cys Tyr Ala Pro Ala Leu Pro Ser Cys Lys Glu Asp Glu Tyr Pro
        35                  40                  45

Val Gly Ser Glu Cys Cys Pro Lys Cys Ser Pro Gly Tyr Arg Val Lys
    50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
            100                 105                 110

Arg Thr Glu Asn Ala Val Cys Gly Cys Ser Pro Gly His Phe Cys Ile
        115                 120                 125

Val Gln Asp Gly Asp His Cys Ala Ala Cys Arg Ala Tyr Ala Thr Ser
    130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Ser Trp Leu Val Thr Lys Ala
            180                 185                 190

Gly Ala Gly Thr Ser Ser Ser His Trp Val Trp Trp Phe Leu Ser Gly
        195                 200                 205

Ser Leu Val Ile Val Ile Val Cys Ser Thr Val Gly Leu Ile Ile Cys
    210                 215                 220

Val Lys Arg Arg Lys Pro Arg Gly Asp Val Val Lys Val Ile Val Ser
225                 230                 235                 240

Val Gln Arg Lys Arg Gln Glu Ala Glu Gly Glu Ala Thr Val Ile Glu
                245                 250                 255
```

```
Ala Leu Gln Ala Pro Pro Asp Val Thr Thr Val Ala Val Glu Glu Thr
            260                 265                 270

Ile Pro Ser Phe Thr Gly Arg Ser Pro Asn His
        275                 280


<210> SEQ ID NO 2
<211> LENGTH: 228
<212> TYPE: PRT
<213> ORGANISM: Homo sapiens

<400> SEQUENCE: 2

Met Pro Val Lys Gly Gly Thr Lys Cys Ile Lys Tyr Leu Leu Phe Gly
1               5                   10                  15

Phe Asn Phe Ile Phe Trp Leu Ala Gly Ile Ala Val Leu Ala Ile Gly
            20                  25                  30

Leu Trp Leu Arg Phe Asp Ser Gln Thr Lys Ser Ile Phe Glu Gln Glu
        35                  40                  45

Thr Asn Asn Asn Asn Ser Ser Phe Tyr Thr Gly Val Tyr Ile Leu Ile
    50                  55                  60

Gly Ala Gly Ala Leu Met Met Leu Val Gly Phe Leu Gly Cys Cys Gly
65                  70                  75                  80

Ala Val Gln Glu Ser Gln Cys Met Leu Gly Leu Phe Phe Gly Phe Leu
                85                  90                  95

Leu Val Ile Phe Ala Ile Glu Ile Ala Ala Ala Ile Trp Gly Tyr Ser
            100                 105                 110

His Lys Asp Glu Val Ile Lys Glu Val Gln Glu Phe Tyr Lys Asp Thr
        115                 120                 125

Tyr Asn Lys Leu Lys Thr Lys Asp Glu Pro Gln Arg Glu Thr Leu Lys
    130                 135                 140

Ala Ile His Tyr Ala Leu Asn Cys Cys Gly Leu Ala Gly Gly Val Glu
145                 150                 155                 160

Gln Phe Ile Ser Asp Ile Cys Pro Lys Lys Asp Val Leu Glu Thr Phe
                165                 170                 175

Thr Val Lys Ser Cys Pro Asp Ala Ile Lys Glu Val Phe Asp Asn Lys
            180                 185                 190

Phe His Ile Ile Gly Ala Val Gly Ile Gly Ile Ala Val Val Met Ile
        195                 200                 205

Phe Gly Met Ile Phe Ser Met Ile Leu Cys Cys Ala Ile Arg Arg Asn
    210                 215                 220

Arg Glu Met Val
225


<210> SEQ ID NO 3
<211> LENGTH: 10
<212> TYPE: PRT
<213> ORGANISM: Artificial Sequence
<220> FEATURE:
<223> OTHER INFORMATION: CDR-H1 VR7660

<400> SEQUENCE: 3

Gly Phe Ser Leu Ser Thr Tyr Asp Met Ile
1               5                   10


<210> SEQ ID NO 4
<211> LENGTH: 16
<212> TYPE: PRT
<213> ORGANISM: Artificial Sequence
<220> FEATURE:
<223> OTHER INFORMATION: CDR-H2 VR7660
```

<400> SEQUENCE: 4

Val Ile Thr Lys Thr Thr Thr Thr Tyr Tyr Ala Asn Trp Ala Lys Gly
1 5 10 15

<210> SEQ ID NO 5
<211> LENGTH: 12
<212> TYPE: PRT
<213> ORGANISM: Artificial Sequence
<220> FEATURE:
<223> OTHER INFORMATION: CDR-H3 VR7660

<400> SEQUENCE: 5

Asp Ala Asp Asp Ala Val Tyr Tyr Tyr Phe Asp Ile
1 5 10

<210> SEQ ID NO 6
<211> LENGTH: 11
<212> TYPE: PRT
<213> ORGANISM: Artificial Sequence
<220> FEATURE:
<223> OTHER INFORMATION: CDR-L1

<400> SEQUENCE: 6

Gln Ala Ser Gln Ser Ile Gly Ser Gly Leu Ala
1 5 10

<210> SEQ ID NO 7
<211> LENGTH: 7
<212> TYPE: PRT
<213> ORGANISM: Artificial Sequence
<220> FEATURE:
<223> OTHER INFORMATION: CDR-L2 VR7660

<400> SEQUENCE: 7

Ala Ala Ser Thr Leu Thr Ser
1 5

<210> SEQ ID NO 8
<211> LENGTH: 12
<212> TYPE: PRT
<213> ORGANISM: Artificial Sequence
<220> FEATURE:
<223> OTHER INFORMATION: CDR-L3 VR7660

<400> SEQUENCE: 8

Gln Glu Gly Val Ser Arg Gly Asn Ile Asp Asn Ala
1 5 10

<210> SEQ ID NO 9
<211> LENGTH: 10
<212> TYPE: PRT
<213> ORGANISM: Artificial Sequence
<220> FEATURE:
<223> OTHER INFORMATION: CDR-H1 VR7272

<400> SEQUENCE: 9

Gly Phe Ser Leu Ser Ser Tyr Ala Met Gly
1 5 10

<210> SEQ ID NO 10
<211> LENGTH: 16
<212> TYPE: PRT
<213> ORGANISM: Artificial Sequence
<220> FEATURE:
<223> OTHER INFORMATION: CDR-H2 VR7272

<400> SEQUENCE: 10

Ala Ile Gly Ser Ile Thr Ala Thr Gly Tyr Ala Arg Trp Ala Lys Gly
1 5 10 15

<210> SEQ ID NO 11
<211> LENGTH: 12
<212> TYPE: PRT
<213> ORGANISM: Artificial Sequence
<220> FEATURE:
<223> OTHER INFORMATION: CDR-H3 VR7272

<400> SEQUENCE: 11

Glu Ile Tyr Val Gly Ser Ala Tyr Ala Phe Asp Ile
1 5 10

<210> SEQ ID NO 12
<211> LENGTH: 11
<212> TYPE: PRT
<213> ORGANISM: Artificial Sequence
<220> FEATURE:
<223> OTHER INFORMATION: CDR-L1 VR7272

<400> SEQUENCE: 12

Gln Ala Ser Gln Ser Ile Ser Asn Tyr Leu Ala
1 5 10

<210> SEQ ID NO 13
<211> LENGTH: 7
<212> TYPE: PRT
<213> ORGANISM: Artificial Sequence
<220> FEATURE:
<223> OTHER INFORMATION: CDR-L2 VR7272

<400> SEQUENCE: 13

Leu Ala Ser Thr Leu Ala Ser
1 5

<210> SEQ ID NO 14
<211> LENGTH: 11
<212> TYPE: PRT
<213> ORGANISM: Artificial Sequence
<220> FEATURE:
<223> OTHER INFORMATION: CDR-L3 VR7272

<400> SEQUENCE: 14

Gln Gln Gly Tyr Ile Asp Asn Val Asn Lys Gly
1 5 10

<210> SEQ ID NO 15
<211> LENGTH: 117
<212> TYPE: PRT
<213> ORGANISM: Artificial Sequence
<220> FEATURE:
<223> OTHER INFORMATION: VH VR7660

<400> SEQUENCE: 15

Gln Ser Val Glu Glu Ser Gly Gly Arg Leu Val Thr Pro Gly Thr Pro
1 5 10 15

Leu Thr Leu Thr Cys Thr Val Ala Gly Phe Ser Leu Ser Thr Tyr Asp
20 25 30

Met Ile Trp Val Arg Gln Ala Pro Gly Lys Gly Leu Glu Tyr Ile Gly
35 40 45

Val Ile Thr Lys Thr Thr Thr Thr Tyr Tyr Ala Asn Trp Ala Lys Gly
50 55 60

Arg Phe Thr Ile Ser Lys Thr Ser Thr Thr Val Asp Leu Lys Met Thr
65 70 75 80

Ser Pro Thr Thr Glu Asp Thr Ala Thr Tyr Phe Cys Ala Arg Asp Ala
85 90 95

Asp Asp Ala Val Tyr Tyr Tyr Phe Asp Ile Trp Gly Pro Gly Thr Leu
100 105 110

Val Thr Val Ser Ser
115

<210> SEQ ID NO 16
<211> LENGTH: 424
<212> TYPE: DNA
<213> ORGANISM: Artificial Sequence
<220> FEATURE:
<223> OTHER INFORMATION: VH nucl VR7660

<400> SEQUENCE: 16
aagcttcgaa gccaccatgg agactgggct gcgctggctt ctcctggtcg ctgtgctcaa 60
aggtgtccag tgtcagtcgg tggaggagtc cgggggtcgc ctggtcacgc ctgggacacc 120
cctgacactc acctgcacgg tcgctggatt ctccctcagt acctacgaca tgatctgggt 180
ccgccaggct ccagggaagg ggctggaata catcggagtc attactaaaa ctactaccac 240
atactacgcg aactgggcga aaggccgatt caccatctcc aaaacctcga ccacggtgga 300
tctgaaaatg accagtccga caaccgagga cacggccacc tatttctgtg ccagagatgc 360
tgatgatgct gtttattact actttgacat ctggggccca ggcaccctgg tcaccgtctc 420
gagt 424

<210> SEQ ID NO 17
<211> LENGTH: 110
<212> TYPE: PRT
<213> ORGANISM: Artificial Sequence
<220> FEATURE:
<223> OTHER INFORMATION: VL VR7660

<400> SEQUENCE: 17

Ala Tyr Asp Met Thr Gln Thr Pro Ala Ser Ala Glu Val Ala Val Gly
1 5 10 15

Gly Thr Val Thr Ile Asn Cys Gln Ala Ser Gln Ser Ile Gly Ser Gly
20 25 30

Leu Ala Trp Tyr Gln Gln Lys Pro Gly Gln Arg Pro Lys Leu Leu Ile
35 40 45

Tyr Ala Ala Ser Thr Leu Thr Ser Gly Val Ser Ser Arg Phe Lys Gly
50 55 60

Ser Gly Ser Gly Thr Glu Phe Thr Leu Thr Ile Ser Gly Val Glu Cys
65 70 75 80

Ala Asp Ala Ala Thr Tyr Tyr Cys Gln Glu Gly Val Ser Arg Gly Asn
85 90 95

Ile Asp Asn Ala Phe Gly Gly Gly Thr Glu Val Val Val Lys
100 105 110

<210> SEQ ID NO 18
<211> LENGTH: 418
<212> TYPE: DNA
<213> ORGANISM: Artificial Sequence
<220> FEATURE:
<223> OTHER INFORMATION: VL nucl VR7660

<400> SEQUENCE: 18
aagcttcgaa gccaccatgg acatgagggc ccccactcag ctgctggggc tcctgctgct 60
ctggctccca ggtgccagat gtgcctatga tatgacccag actccagcct ctgcggaggt 120
agctgtggga ggcacagtca ccatcaattg ccaggccagt cagagcattg gcagtggttt 180
ggcctggtat cagcagaaac cagggcagcg tcccaaactc ctgatctatg ctgcatccac 240
tctgacatct ggggtctcat cgcggttcaa aggcagtgga tctgggacag agttcactct 300
caccatcagc ggcgtggagt gtgccgatgc tgccacttac tactgtcaag agggtgttag 360
tcgtggtaat attgataatg ccttcggcgg agggaccgag gtggtggtca aacgtacg 418

<210> SEQ ID NO 19
<211> LENGTH: 117
<212> TYPE: PRT
<213> ORGANISM: Artificial Sequence
<220> FEATURE:
<223> OTHER INFORMATION: VH VR7272

<400> SEQUENCE: 19

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Gly Trp Val Arg Gln Ala Pro Gly Lys Gly Leu Glu Trp Ile Gly
        35                  40                  45

Ala Ile Gly Ser Ile Thr Ala Thr Gly Tyr Ala Arg Trp Ala Lys Gly
    50                  55                  60

Arg Phe Ser Ile Ser Lys Thr Ser Thr Thr Val Asp Leu Lys Met Thr
65                  70                  75                  80

Ser Pro Thr Thr Glu Asp Thr Ala Thr Tyr Phe Cys Ala Arg Glu Ile
                85                  90                  95

Tyr Val Gly Ser Ala Tyr Ala Phe Asp Ile Trp Gly Pro Gly Thr Leu
            100                 105                 110

Val Thr Val Ser Ser
        115

<210> SEQ ID NO 20
<211> LENGTH: 424
<212> TYPE: DNA
<213> ORGANISM: Artificial Sequence
<220> FEATURE:
<223> OTHER INFORMATION: VH nucl VR7272

<400> SEQUENCE: 20
aagcttcgaa gccaccatgg agactgggct gcgctggctt ctcctggtcg ctgtgctcaa 60
aggtgtccag tgtcagtcgc tggaggagtc cgggggtcgc ctggtcacgc ctgggacacc 120
cctgacactc acctgcacag tctctggatt ctccctcagt agctatgcaa tgggctgggt 180
ccgccaggct ccagggaagg ggctggagtg gatcggagcc attggtagta ttactgccac 240
tggctacgcg cgctgggcaa aaggccgatt cagcatctcc aagacctcga ccacggtgga 300
tctgaaaatg accagtccga caaccgagga cacggccacc tatttctgtg ccagagagat 360
ttatgttggg tctgcttatg cctttgacat ctggggccca ggcaccctgg tcaccgtctc 420
gagt 424

<210> SEQ ID NO 21
<211> LENGTH: 109
<212> TYPE: PRT
<213> ORGANISM: Artificial Sequence -continued

```
<220> FEATURE:
<223> OTHER INFORMATION: VL VR7272

<400> SEQUENCE: 21

Ala Tyr Asp Met Thr Gln Thr Pro Ala Ser Val Glu Val Ala Val Gly
1               5                   10                  15

Asp Thr Val Thr Ile Lys Cys Gln Ala Ser Gln Ser Ile Ser Asn Tyr
            20                  25                  30

Leu Ala Trp Tyr Gln Gln Lys Pro Gly Gln Pro Pro Lys Leu Leu Ile
        35                  40                  45

Tyr Leu Ala Ser Thr Leu Ala Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Gln Gly Tyr Ile Asp Asn Val
                85                  90                  95

Asn Lys Gly Phe Gly Gly Gly Thr Glu Val Val Val Lys
            100                 105


<210> SEQ ID NO 22
<211> LENGTH: 415
<212> TYPE: DNA
<213> ORGANISM: Artificial Sequence
<220> FEATURE:
<223> OTHER INFORMATION: VL nucl VR7272

<400> SEQUENCE: 22

aagcttcgaa gccaccatgg acacgagggc ccccactcag ctgctggggc tcctgctgct      60

ctggctccca ggtgccagat gtgcctatga tatgacccag actccagcct ctgtggaggt     120

agctgtggga gacactgtca ccatcaagtg tcaggccagt cagagcatta gtaactactt     180

agcctggtat cagcagaaac cagggcagcc tcccaagctc ctgatctatc tggcatctac     240

tctggcatct ggggtcccat cgcggttcaa aggcagtgga tctgggacag agttcactct     300

caccatcagc gacctggagt gtgccgatgc tgccacttac tattgtcaac agggttatat     360

tgataatgtt aataaaggtt tcggcggagg gaccgaggtg gtggtcaaac gtacg          415
```

BISPECIFIC ANTIBODIES BINDING HVEM AND CD9

FIELD OF THE INVENTION

The present invention belongs to the field of multispecific antibodies binding at least HVEM and CD9, and their uses in the treatment of cancer and/or infectious diseases.

BACKGROUND OF THE INVENTION

T-cells are key to a successful cell-mediated immune response necessary to eliminate cancer cells, bacteria and viruses. They recognise antigens displayed on the surface of tumour cells or antigens from bacteria and viruses replicating within the cells or from pathogens or pathogen products endocytosed from the extracellular fluid. T-cells have two major roles. They can become cytotoxic T-cells capable of destroying cells marked as foreign. Cytotoxic T-cells have a unique surface protein called CD8, thus they are often referred to as CD8+ T-cells. Alternatively, T-cells can become helper T-cells, which work to regulate and coordinate the immune system. Helper T-cells have a unique surface protein called CD4 and are thus often called CD4+ T-cells. Helper T-cells have several important roles in the immune system: 1) responding to activation by specific antigens by rapidly proliferating; 2) signaling B cells to produce antibodies; and 3) activating macrophages.

Cancer eludes the immune system by exploiting mechanisms developed to avoid auto-immunity. However, the immune system is programmed to avoid immune over-activation which could harm healthy tissue. T-cell activation is at the core of these mechanisms. Antigen specific T-cells normally able to fight disease can become functionally tolerant (exhausted) to infectious agents or tumour cells by over stimulation or exposure to suppressive molecules. Therefore, molecules that enhance the natural function of T-cells or overcome suppression of T-cells have great utility in the treatment or prevention of cancer and infectious disease.

Naïve T-cells are immature T-cells which are yet to have encountered antigen specific to their T-cell receptor, while memory T-cells have previously encountered antigen specific to their receptor and matured into effector cells, and as such can rapidly respond when the same antigen is presented. A key surface marker for identifying this change is the switch from the expression of CD45RA on naïve T-cells to CD45RO on memory T-cells, and measuring the level of these cell surface proteins allows for the identification of the two populations. The immune system can identify tumour antigens, and mount a response, leading to the generation of memory T-cells. However, the tumour microenvironment can dampen this response through multiple mechanisms, leading to tumour progression. The activation of these memory T-cells therefore offers great therapeutic value in reversing the immunosuppressive function of the tumour microenvironment.

In recent years, immunotherapy has become an established treatment option for an increasing number of cancer patients, exemplified by the increased use of therapeutic antibody-based immune checkpoint inhibitors (CPI's). This has arisen from an increased immunological understanding of how cancer cells perturb immune cell activation by hijacking pathways normally involved in maintaining tolerance and skewing the balance between co-stimulation and co-inhibition (Chen and Mellman., Immunity. 39:1-105 (2013)). Amongst the pathways that have emerged as key regulators in this regard, include CTLA-4 and the PD-1/PD-L1 checkpoint molecules serving to down-regulate T cell and myeloid cell activation in the tumour microenvironment. Ipilimumab (anti-CTLA-4) was the first CPI to be approved in 2011 as a treatment for melanoma, closely followed by FDA approval of anti-PD1 directed antibodies, pembrolizumab and nivolumab in 2014 (Hargadon et al., International Immunopharmacol. 62:29-39 (2018)). There are still significant challenges in understanding differences in efficacy across patient groups, ranging from complete responses, to treatment relapse and even failure to respond, (Haslam and Prasad. JAMA Network Open. 5:2e192535 (2019)).

Despite the promising anti-tumour efficacy of several monoclonal antibodies, many cancers are refractory to treatments with a single antibody. Combinations of two or more antibodies are currently being tested in patients to provide improved methods of treatment. To date, these therapies rely on rational design of known mechanisms of action and are largely based on combining antigen-specificities known to be independently effective in the treatment of cancer, either as combination therapies or in a bispecific antibody format. This state of the art approach is a limiting factor in the development of new therapies as it relies on known therapies.

Therefore, there is still the need to identify novel modulators of T-cell activation based on unbiased biology, which allows identification of novel target pairs capable of enhancing, T-cell activation and induction of T-cell proliferation for the treatment of cancer and infectious diseases.

SUMMARY OF THE INVENTION

The present invention addresses the above-identified need by providing in a first aspect an antibody which comprises a first antigen-binding portion binding HVEM and a second antigen-binding portion binding CD9.

In one embodiment of this first aspect, each of the antigen-binding portions of the antibody which comprises a first antigen-binding portion binding HVEM and a second antigen-binding portion binding CD9 is a monoclonal antigen-binding portion.

In another embodiment, each of the antigen-binding portions is independently selected from a Fab, a Fab', a scFv or a VH H. In yet another aspect, the antigen-binding portions are the antigen-binding portions of an IgG.

In another embodiment, the antibody which comprises a first antigen-binding portion binding HVEM and a second antigen-binding portion binding CD9, is chimeric, human or humanised, and preferably the antibody is humanised.

In another embodiment, the antibody comprises a heavy chain constant region selected from an IgG1, an IgG2, IgG3 or an IgG4 isotype, or a variant thereof.

In another embodiment, the antibody further comprises at least an additional antigen-binding portion. The additional antigen-binding portion may be capable of increasing the half-life of the antibody. Preferably the additional antigen-binding portion binds albumin, more preferably human serum albumin.

In one embodiment, the second antigen binding portion binds CD9 in CD9 loop 2, wherein preferably the second antigen-binding portion binds within amino acids 112 to 195 of SEQ ID NO: 2.

In another embodiment, the first antigen-binding portion binding HVEM of the antibody according to the invention comprises a first heavy chain variable region and a first light chain variable region and the second antigen-binding portion binding CD9 comprises a second heavy chain variable region and a second light chain variable region and wherein:

a. The first heavy chain variable region comprises a CDR-H1 comprising SEQ ID NO: 3, a CDR-H2 comprising SEQ ID NO: 4 and a CDR-H3 comprising SEQ ID NO: 5; and
b. The first light chain variable region comprises a CDR-L1 comprising SEQ ID NO: 6, a CDR-L2 comprising SEQ ID NO: 7 and a CDR-L3 comprising SEQ ID NO: 8; and
c. The second heavy chain variable region comprises a CDR-H1 comprising SEQ ID NO: 9, a CDR-H2 comprising SEQ ID NO: 10 and a CDR-H3 comprising SEQ ID NO: 11; and
d. The second light chain variable region comprises a CDR-L1 comprising SEQ ID NO: 12, a CDR-L2 comprising SEQ ID NO: 13 and a CDR-L3 comprising SEQ ID NO: 14;

or e. The first heavy chain variable region comprises SEQ ID NO: 15 and the first light chain variable region comprises SEQ ID NO: 17; and the second heavy chain variable region comprises SEQ ID NO: 19 and second light chain variable region comprises SEQ ID NO: 21;

or f. The first heavy chain variable region is encoded by a nucleotide sequence comprising SEQ ID NO: 16 and the first light chain variable region is encoded by a nucleotide sequence comprising SEQ ID NO: 18; and the second heavy chain variable region is encoded by a nucleotide sequence comprising SEQ ID NO: 20 and second light chain variable region is encoded by a nucleotide sequence comprising SEQ ID NO: 22.

In a second aspect of the present invention there is provided a pharmaceutical composition comprising the antibody according to the first aspect of the invention and all its embodiments and one or more pharmaceutically acceptable excipients.

In a third aspect, the invention provides for the antibody according to the first aspect of the invention and all its embodiments or the pharmaceutical composition according to the second aspect of the invention and all its embodiments for use in therapy.

In one embodiment of this third aspect, the use is for the treatment of cancer and/or an infectious disease. In another embodiment, the antibody or the composition according to the invention and all its embodiments are for use in the treatment of cancer concomitantly or sequentially to one or more additional cancer therapies.

In a fourth aspect of the present invention, there is provided for a method for treating a subject afflicted with cancer and/or an infectious disease, comprising administering to the subject a pharmaceutically effective amount of the antibody according to the first aspect of the invention and all its embodiments or the pharmaceutical composition according to the second aspect of the invention and all its embodiments.

In one embodiment of this fourth aspect, the antibody or the composition are administered concomitantly or sequentially to one or more additional cancer therapies.

In a fifth aspect, the invention provides for the use of an antibody according to the first aspect of the invention and all its embodiments or the pharmaceutical composition according to the second aspect of the invention and all its embodiments in the manufacture of a medicament for treating cancer.

In one embodiment of this fifth aspect, the antibody or the composition are administered concomitantly or sequentially to one or more additional cancer therapies.

DETAILED DESCRIPTION OF THE INVENTION

Figure 1:
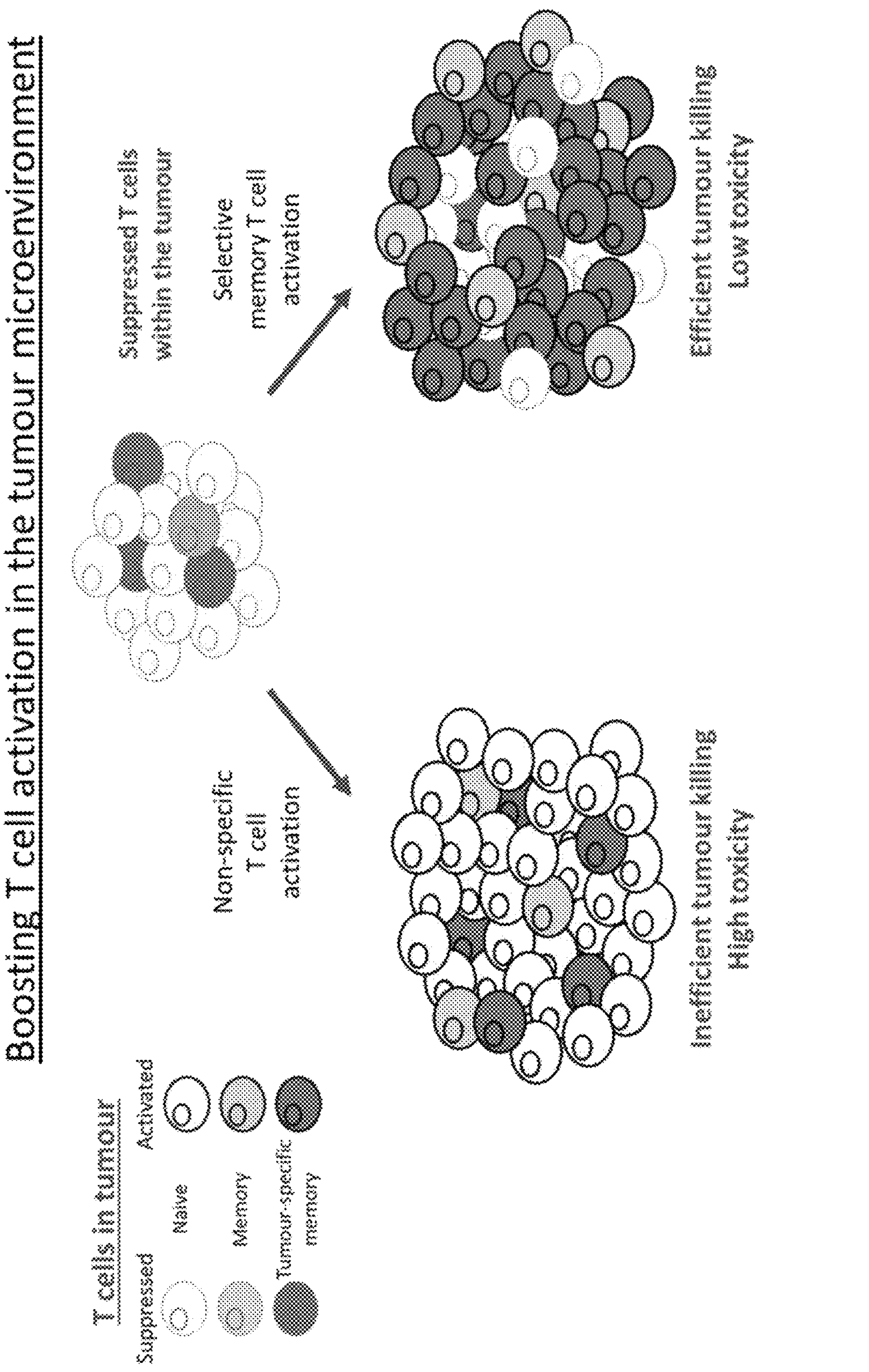
FIG. 1. Schematic representation of acquired immune resistance through selective memory T-cell activation versus non-specific T-cell activation.

The present invention will now be described with respect to particular non-limiting aspects and embodiments thereof and with reference to certain figures and examples.

Technical terms are used by their common sense unless indicated otherwise. If a specific meaning is conveyed to certain terms, definitions of terms will be given in the context of which the terms are used.

Where the term "comprising" is used in the present description and claims, it does not exclude other elements. For the purposes of the present disclosure, the term "consisting of" is considered to be a preferred embodiment of the term "comprising of".

Where an indefinite or definite article is used when referring to a singular noun, e.g. "a", "an" or "the", this includes a plural of that noun unless something else is specifically stated.

As used herein, the terms "treatment", "treating" and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. Treatment thus covers any treatment of a disease in a mammal, particularly in a human, and includes: (a) preventing the disease from occurring in a subject, i.e. a human, which may be predisposed to the disease but has not yet been diagnosed as having it; (b) inhibiting the disease, i.e., arresting its development; and (c) relieving the disease, i.e., causing regression of the disease.

A "therapeutically effective amount" refers to the amount of antibody comprising the distinct antigen-binding portions binding HVEM and CD9 that, when administered to a mammal or other subject for treating a disease, is sufficient to affect such treatment for the disease.

The present invention provides for antibodies comprising a first antigen-binding portion binding HVEM and a second antigen-binding portion binding CD9. The first and the second antigen-binding portions are located in the same antibody, i.e. they are part of the same polypeptide chain and/or associate via one or more covalent and/or non-covalent associations (such as the screening format Fab-Kd-Fab described herein or the classic heavy and light chain association forming a full IgG antibody) or are covalently linked so as to form one single molecule (such as cross-linking two separately expressed polypeptide chains, optionally via specific cross-linking agents).

The herpes virus entry mediator (HVEM) is a member of the tumour necrosis factor receptor superfamily (TNFRSF), and it is also known as TNFRSFI4 or CD270 (Uniprot accession reference Q92956). HVEM is a bidirectional switch regulating T-cell activation in a costimulatory or coinhibitory fashion, whose outcome depends on the binding partner. HVEM can act as both receptor and ligand, the binding of endogenous ligand LIGHT or agonist antibodies to HVEM delivers a costimulatory signal; whereas the binding of HVEM to BTLA (IgSF) or CD160 on Effector T-cells delivers a coinhibitory signal. The sequence of human HVEM, including the signal peptide is shown as SEQ ID NO: 1 (Table 1).

CD9 and in particular human CD9 (Uniprot accession number P21926) was discovered as a human B-lymphocyte differentiation antigen and it has been found to be widely expressed on many non-hematopoietic tissues including various cancer. It is also known as Tetraspanin-29, motility-related protein-1, 5H9 antigen, cell growth-inhibiting gene 2 protein, leukocyte antigen MIC3 and MRP-1 (Rappa et al., Oncotarget 6:10, 7970-7991 (2015)). CD9 is a tetraspanin that is broadly expressed in a variety of solid tissues and on a multitude of hematopoietic cells (Nature reviews Cancer (9) 40-55 (2009)). CD9 involvement has been shown in the invasiveness and tumorigenicity of human breast cancer cells (Oncotargets, 6:10 (2015)), the suppression of cell motility and metastasis (J. Exp. Med 177:5 (1993)) and to have a role in T cells activation (J. Exp. Med 184:2 (1994)).

CD9 has also been shown to be present in exosomes (Asia-Pac J Clin Oncol, 2018; 1-9). Exosomes are cell derived nanovesicles with size of 30-120 nm. The molecular composition of exosomes reflects their origin and include unique composition of tetraspanins. Exosomes are thoughts to constitute a potent mode of intercellular communication that is important in the immune response, cell-to-cell spread of infectious agents, and tumour progression.

The sequence of human CD9, including the signal peptide is shown as SEQ ID NO:2 (Table 1).

TABLE 1

| | |
|---|---|
| SEQ ID NO: 1<br>Human HVEM | MEPPGDWGPPPWRSTPKTDVLRLVLYLTFLGAPCYAPALPSCKEDEY<br>PVGSECCPKCSPGYRVKEACGELTGTVCEPCPPGTYIAHLNGLSKCLQ<br>CQMCDPAMGLRASRNCSRTENAVCGCSPGHFCIVQDGDHCAACRAY<br>ATSSPGQRVQKGGTESQDTLCQNCPPGTFSPNGTLEECQHQTKCSW<br>LVTKAGAGTSSSHWVWWFLSGSLVIVIVCSTVGLIICVKRRKPRGDVVK<br>VIVSVQRKRQEAEGEATVIEALQAPPDVTTVAVEETIPSFTGRSPNH |
| SEQ ID NO: 2<br>Human CD9 | MPVKGGTKCIKYLLFGFNFIFWLAGIAVLAIGLWLRFDSQTKSIFEQETN<br>NNNSSFYTGVYILIGAGALMMLVGFLGCCGAVQESQCMLGLFFGFLLVI<br>FAIEIAAAIWGYSHKDEVIKEVQEFYKDTYNKLKTKDEPQRETLKAIHYAL<br>NCCGLAGGVEQFISDICPKKDVLETFTVKSCPDAIKEVFDNKFHIIGAVGI<br>GIAVVMIFGMIFSMILCCAIRRNREMV |
| SEQ ID NO: 3<br>CDR-H1<br>VR7660 | GFSLSTYDMI |
| SEQ ID NO: 4<br>CDR-H2<br>VR7660 | VITKTTTTYYANWAKG |
| SEQ ID NO: 5<br>CDR-H3<br>VR7660 | DADDAVYYYFDI |
| SEQ ID NO: 6<br>CDR-L1<br>VR7660 | QASQSIGSGLA |
| SEQ ID NO: 7<br>CDR-L2<br>VR7660 | AASTLTS |
| SEQ ID NO: 8<br>CDR-L3<br>VR7660 | QEGVSRGNIDNA |
| SEQ ID NO: 9<br>CDR-H1<br>VR7272 | GFSLSSYAMG |
| SEQ ID NO: 10<br>CDR-H2<br>VR7272 | AIGSITATGYARWAKG |
| SEQ ID NO: 11<br>CDR-H3<br>VR7272 | EIYVGSAYAFDI |

TABLE 1-continued

| | |
|---|---|
| SEQ ID NO: 12<br>CDR-L1<br>VR7272 | QASQSISNYLA |
| SEQ ID NO: 13<br>CDR-L2<br>VR7272 | LASTLAS |
| SEQ ID NO: 14<br>CDR-L3<br>VR7272 | QQGYIDNVNKG |
| SEQ ID NO: 15<br>VH VR7660 | QSVEESGGRLVTPGTPLTLTCTVAGFSLSTYDMIWVRQAPGKGLEYIG<br>VITKTTTTYYANWAKGRFTISKTSTTVDLKMTSPTTEDTATYFCARDAD<br>DAVYYYFDIWGPGTLVTVSS |
| SEQ ID NO: 16<br>VH nucl.<br>VR7660 | AAGCTTCGAAGCCACCATGGAGACTGGGCTGCGCTGGCTTCTCCTG<br>GTCGCTGTGCTCAAAGGTGTCCAGTGTCAGTCGGTGGAGGAGTCC<br>GGGGGTCGCCTGGTCACGCCTGGGACACCCCTGACACTCACCTGC<br>ACGGTCGCTGGATTCTCCCTCAGTACCTACGACATGATCTGGGTCC<br>GCCAGGCTCCAGGGAAGGGGCTGGAATACATCGGAGTCATTACTAA<br>AACTACTACCACATACTACGCGAACTGGGCGAAAGGCCGATTCACC<br>ATCTCCAAAACCTCGACCACGGTGGATCTGAAAATGACCAGTCCGA<br>CAACCGAGGACACGGCCACCTATTTCTGTGCCAGAGATGCTGATGA<br>TGCTGTTTATTACTACTTTGACATCTGGGGCCCAGGCACCCTGGTCA<br>CCGTCTCGAGT |
| SEQ ID NO: 17<br>VL VR7660 | AYDMTQTPASAEVAVGGTVTINCQASQSIGSGLAWYQQKPGQRPKLLI<br>YAASTLTSGVSSRFKGSGSGTEFTLTISGVECADAATYYCQEGVSRGNI<br>DNAFGGGTEVVVK |
| SEQ ID NO: 18<br>VL nucl.<br>VR7660 | AAGCTTCGAAGCCACCATGGACATGAGGGCCCCCACTCAGCTGCTG<br>GGGCTCCTGCTGCTCTGGCTCCCAGGTGCCAGATGTGCCTATGATA<br>TGACCCAGACTCCAGCCTCTGCGGAGGTAGCTGTGGGAGGCACAG<br>TCACCATCAATTGCCAGGCCAGTCAGAGCATTGGCAGTGGTTTGGC<br>CTGGTATCAGCAGAAACCAGGGCAGCGTCCCAAACTCCTGATCTAT<br>GCTGCATCCACTCTGACATCTGGGGTCTCATCGCGGTTCAAAGGCA<br>GTGGATCTGGGACAGAGTTCACTCTCACCATCAGCGGCGTGGAGTG<br>TGCCGATGCTGCCACTTACTACTGTCAAGAGGGTGTTAGTCGTGGT<br>AATATTGATAATGCCTTCGGCGGAGGGACCGAGGTGGTGGTCAAAC<br>GTACG |
| SEQ ID NO: 19<br>VH VR7272 | QSLEESGGRLVTPGTPLTLTCTVSGFSLSSYAMGWVRQAPGKGLEWI<br>GAIGSITATGYARWAKGRFSISKTSTTVDLKMTSPTTEDTATYFCAREIY<br>VGSAYAFDIWGPGTLVTVSS |
| SEQ ID NO: 20<br>VH nucl.<br>VR7272 | AAGCTTCGAAGCCACCATGGAGACTGGGCTGCGCTGGCTTCTCCTG<br>GTCGCTGTGCTCAAAGGTGTCCAGTGTCAGTCGCTGGAGGAGTCC<br>GGGGGTCGCCTGGTCACGCCTGGGACACCCCTGACACTCACCTGC<br>ACAGTCTCTGGATTCTCCCTCAGTAGCTATGCAATGGGCTGGGTCC<br>GCCAGGCTCCAGGGAAGGGGCTGGAGTGGATCGGAGCCATTGGTA<br>GTATTACTGCCACTGGCTACGCGCGCTGGGCAAAAGGCCGATTCAG<br>CATCTCCAAGACCTCGACCACGGTGGATCTGAAAATGACCAGTCCG<br>ACAACCGAGGACACGGCCACCTATTTCTGTGCCAGAGAGATTTATG<br>TTGGGTCTGCTTATGCCTTTGACATCTGGGGCCCAGGCACCCTGGT<br>CACCGTCTCGAGT |
| SEQ ID NO: 21<br>VL VR7272 | AYDMTQTPASVEVAVGDTVTIKCQASQSISNYLAWYQQKPGQPPKLLIY<br>LASTLASGVPSRFKGSGSGTEFTLTISDLECADAATYYCQQGYIDNVNK<br>GFGGGTEVVVK |
| SEQ ID NO: 22<br>VL nucl.<br>VR7272 | AAGCTTCGAAGCCACCATGGACACGAGGGCCCCCACTCAGCTGCT<br>GGGGCTCCTGCTGCTCTGGCTCCCAGGTGCCAGATGTGCCTATGAT<br>ATGACCCAGACTCCAGCCTCTGTGGAGGTAGCTGTGGGAGACACTG<br>TCACCATCAAGTGTCAGGCCAGTCAGAGCATTAGTAACTACTTAGCC<br>TGGTATCAGCAGAAACCAGGGCAGCCTCCCAAGCTCCTGATCTATC<br>TGGCATCTACTCTGGCATCTGGGGTCCCATCGCGGTTCAAAGGCAG<br>TGGATCTGGGACAGAGTTCACTCTCACCATCAGCGACCTGGAGTGT<br>GCCGATGCTGCCACTTACTATTGTCAACAGGGTTATATTGATAATGT<br>TAATAAAGGTTTCGGCGGAGGGACCGAGGTGGTGGTCAAACGTAC<br>G |

Within the present invention, unless recited otherwise, human HVEM and CD9 are always intended to be included in the term "HVEM" and CD9". However, unless "human HVEM" and/or "human CD9" are explicitly used, the terms "HVEM" and/or "CD9" include the same targets in other species, especially non-primate (e.g. rodents) and non-human primate (such as cynomolgus monkey) species.

The present invention therefore provides for an antibody comprising a first antigen-binding portion binding human HVEM and a second antigen-binding portion binding human CD9. The first and the second antigen-binding portions are located on the same antibody, i.e. they are part of the same polypeptide chain, they associate via one or more non-covalent and/or covalent associations or are linked so as to form one single molecule.

The present invention also provides for an antibody comprising a first antigen-binding portion binding an extracellular domain region of human HVEM and a second antigen-binding portion binding an extracellular domain region of human CD9.

In particular, there is provided an antibody comprising a first antigen-binding portion binding human HVEM as defined in SEQ ID NO: 1 or from amino acid 39 to 283 of SEQ ID NO: 1 or from amino acid 39 to 202 of SEQ ID NO: 1 and a second antigen-binding portion binding human CD9 as defined in SEQ ID NO: 2 or from amino acid 2 to 228 of SEQ ID NO: 2, alternatively from amino acid 34 to 55 of SEQ ID NO: 2 or alternatively from amino acid 112-195. The first and the second antigen-binding portions are located on the same antibody, i.e. they are part of the same polypeptide chain, they associate via one or more non-covalent and/or covalent associations or are linked so as to form one single molecule.

The monoclonal antibody of the present invention, upon binding of HVEM and CD9, stimulates T-cell activation, i.e. further activates T-cells and enhances induction of T-cell proliferation, and in particular, the monoclonal antibody comprising a first antigen-binding portion binding HVEM and a second antigen-binding portion binding CD9 further activates T-cells and enhances induction of T-cell proliferation in the presence of SEB stimulation. More specifically, the monoclonal antibody comprising a first antigen-binding portion binding HVEM and a second antigen-binding portion binding CD9 further activates T-cells and enhances induction of T-cell proliferation in the presence of SEB stimulation but it does not activate unstimulated T-cells. More specifically, the T-cell is at least a CD4+ T-cell or at least a CD8+ T-cell or a mixture thereof, more preferably a memory CD4+ T-cell or a memory CD8+ T-cell.

The term "activate" (and grammatical variations thereof) as used herein, at least includes the upregulation of specific T-cell markers, i.e. increased transcription and/or translation of these markers and/or trafficking of these newly transcribed/translated markers or of any marker already expressed to the cell membrane, and the induction of proliferation.

Hence, the present invention provides for a monoclonal antibody comprising a first antigen-binding portion binding HVEM and a second antigen-binding portion binding CD9 capable of activating T-cells in the presence of an anti-SEB stimulation wherein the further activation of T-cell is measured as an upregulation of T-cell markers and the enhancement of T-cell proliferation.

For maintaining the ability of the immune system to recognise and mount a response to the almost infinite number of possible foreign peptide antigens, a large repertoire of naïve T-cells is required. When a foreign antigen is encountered—for example as presented on virus infected cells or mutated tumour cells—T-cells of that specificity are selectively expanded to allow killing of the virus or tumour. As part of this selective expansion a number of memory T-cells are formed and retained at increased frequency to allow a rapid response should the same threat be re-encountered. This expansion and maintenance of memory T-cells is the basis of acquired immune resistance.

Stimulation of the cytotoxic activity of T-cells to promote tumour or virus-infected cell killing is a desirable therapeutic approach—but if non-specific can be catastrophic due to massive cytokine release and indiscriminate cell killing (FIG. 1). Agents designed to selectively stimulate these memory T-cells will promote a more specific, localised and effective immune response without overt immune activation and toxicity.

Hence, the present invention provides for a monoclonal antibody comprising a first antigen-binding portion binding HVEM and a second antigen-binding portion binding CD9 capable of further activating memory T-cells, wherein the further activation of T-cell results in an upregulation of T-cell markers and the enhancement of memory T-cell proliferation.

Specific markers of T-cell activation and proliferation include but are not limited to the upregulation of CD25, CD137 and CD71.

In one preferred embodiment of the present invention, the monoclonal antibody comprising a first antigen-binding portion binding HVEM and a second antigen-binding portion binding CD9 is capable of activating T-cells in the presence of SEB stimulation wherein activating T-cell results in an upregulation of CD137, CD71 and CD25.

The term "antibody" as used herein includes whole immunoglobulin molecules and antigen-binding portions of immunoglobulin molecules associated via non-covalent and/or covalent associations or linked together, optionally via a linker.

In one embodiment, the antigen-binding portions binding HVEM and CD9 are the antigen-binding portions of an IgG, wherein one arm binds HVEM and the other arm binds CD9.

In another embodiment, the antigen-biding portions comprised in the antibody are functionally active fragments or derivatives of a whole immunoglobulin and may be, but are not limited to, VH, VL, VHH, Fv, scFv fragment (including dsscFv), Fab fragments, modified Fab fragments, Fab' fragments, $F(ab')_2$ fragments, Fv and epitope-binding fragments of any of the above.

Other antibody fragments include those described in WO2005003169, WO2005003170, WO2005003171, WO2009040562 and WO2010035012. Functionally active fragments or derivative of a whole immunoglobulin and methods of producing them are well known in the art, see for example Verma et al., 1998, Journal of Immunological Methods, 216, 165-181; Adair and Lawson, 2005. Therapeutic antibodies. Drug Design Reviews—Online 2(3):209-217.

In one embodiment of the invention each of the antigen-binding portions is independently selected from a Fab, a Fab', a scFv or a VHH. In one embodiment, the antigen-binding portion binding HVEM is a Fab whilst the antigen-binding portion binding CD9 is a scFv. In another embodiment, the antigen-binding portion binding CD9 is a Fab whilst the antigen-binding portion binding HVEM is a scFv. In another embodiment, both antigen-binding portions are a Fab or scFv.

In one preferred embodiment, the antibody is monoclonal, which means that the antigen-binding portions comprised therein are all monoclonal. Therefore, in one preferred embodiment of the present invention, there is provided a monoclonal antibody comprising a first antigen-binding portion binding HVEM and a second antigen-binding portion binding CD9. Preferably, this antibody is capable of further activating T-cells and/or enhancing induction of T-cell proliferation in the presence of SEB stimulation wherein activating T-cells results in an upregulation of CD71, CD137 and CD25.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., Antibodies for use in the invention may also be generated using single lymphocyte antibody methods by cloning and expressing immunoglobulin variable region cDNAs generated from single lymphocytes selected for the production of specific antibodies by for example the methods described by Babcook, J. et al, 1996, Proc. Natl. Acad. Sci. USA 93(15): 7843-78481; WO92/02551; WO2004/051268 and WO2004/106377.

The antibodies of the present invention can also be generated using various phage display methods known in the art and include those disclosed by Brinkman et al. (in J. Immunol. Methods, 1995, 182: 41-50), Ames et al. (J. Immunol. Methods, 1995, 184: 177-186), Kettleborough et al. (Eur. J. Immunol. 1994, 24:952-958), Persic et al. (Gene, 1997 187 9-18), Burton et al. (Advances in Immunology, 1994, 57: 191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108. When the antigen-binding portions comprised in the antibody are functionally active fragments or derivatives of a whole immunoglobulin such as single chain antibodies, they may be made such as those described in U.S. Pat. No. 4,946,778 which can also be adapted to produce single chain antibodies binding to HVEM and CD9. Transgenic mice, or other organisms, including other mammals, may be used to express antibodies, including those within the scope of the invention.

The antibody of the present invention may be chimeric, human or humanised.

Chimeric antibodies are those antibodies encoded by immunoglobulin genes that have been genetically engineered so that the light and heavy chain genes are composed of immunoglobulin gene segments belonging to different species.

Humanized, antibodies are antibody molecules from non-human species having one or more complementarity determining regions (CDRs) from the non-human species and a framework region from a human immunoglobulin molecule (see, e.g. U.S. Pat. No. 5,585,089; WO91/09967). Preferably the antibody of the present invention is humanised. In one embodiment of the present invention, there is provided an antibody, preferably a monoclonal antibody, comprising a first antigen-binding portion binding HVEM and a second antigen-binding portion binding CD9, wherein the antibody is humanised. More preferably this antibody is capable of activating T-cells and/or enhancing induction of T-cell proliferation in the presence of SEB stimulation wherein activating T-cell results in an upregulation of CD137, CD71 and CD25.

In humanised antibodies, the heavy and/or light chain contains one or more CDRs (including, if desired, one or more modified CDRs) from a donor antibody (e.g. a murine monoclonal antibody) grafted into a heavy and/or light chain variable region framework of an acceptor antibody (e.g. a human antibody). For a review, see Vaughan et al, Nature Biotechnology, 16, 535-539, 1998. In one embodiment, rather than the entire CDR being transferred, only one or more of the specificity determining residues from any one of the CDRs described herein above are transferred to the human antibody framework (see, for example, Kashmiri et al., 2005, Methods, 36, 25-34). When the CDRs or specificity determining residues are grafted, any appropriate acceptor variable region framework sequence may be used having regard to the class/type of the donor antibody from which the CDRs are derived, including mouse, primate and human framework regions. Preferably, the humanised antibody according to the invention comprises a variable domain comprising human acceptor framework regions as well as one or more of the CDRs or specificity determining residues described above. Thus, provided in one embodiment is a humanised monoclonal antibody comprising an antigen-binding portion binding HVEM and an antigen-binding portion binding CD9, wherein each antigen-binding portion comprises a variable domain comprising human acceptor framework regions and non-human donor CDRs.

Examples of human frameworks which can be used in the invention are KOL, NEWM, REI, EU, TUR, TEI, LAY and POM (Kabat et al, supra). For example, KOL and NEWM can be used for the heavy chain, REI can be used for the light chain and EU, LAY and POM can be used for both the heavy chain and the light chain. Alternatively, human germline sequences may be used; these are available at, for example: http://vbase.mrc-cpe.cam.ac.uk/. In a CDR-grafted antibody of the invention, the acceptor heavy and light chains do not necessarily need to be derived from the same antibody and may, if desired, comprise composite chains having framework regions derived from different chains.

Fully human antibodies are those antibodies in which the variable regions and the constant regions (where present) of both the heavy and the light chains are all of human origin, or substantially identical to sequences of human origin, not necessarily from the same antibody. Examples of fully human antibodies may include antibodies produced for example by the phage display methods described above and antibodies produced by mice in which the murine immunoglobulin variable and constant region genes have been replaced by their human counterparts, e.g., as described in general terms in EP0546073, U.S. Pat. Nos. 5,545,806, 5,569,825, 5,625,126, 5,633,425, 5,661,016, 5,770,429, EP 0438474 and EP0463151.

Furthermore, the antibody of the invention may comprise a heavy chain constant region selected from an IgG1, an IgG2, an IgG3 or an IgG4 isotype, or a variant thereof. The constant region domains of the antibody of the invention, if present, may be selected having regard to the proposed function of the antibody, and in particular the effector functions which may be required. For example, the human IgG constant region domains of the IgG1 and IgG3 isotypes may be used when the antibody effector functions are required. Alternatively, IgG2 and IgG4 isotypes may be used when the antibody effector functions are not required. For example, IgG4 molecules in which the serine at position 241 has been changed to proline as described in Angal et al., Molecular Immunology, 1993, 30 (1), 105-108, may be used. Particularly preferred is the IgG4 constant domain that comprises this change.

It should also be appreciated that antigen-binding portions comprised in the antibody of the invention such as the functionally-active fragments or derivatives of whole immunoglobulin fragments described above, may be incorporated into other antibody formats than being the antigen-binding portions of the classic IgG format. Alternative format to the classic IgG may include those known in the art and those described herein, such as DVD-Igs, FabFvs for example as disclosed in WO2009/040562 and WO2010/035012, diabodies, triabodies, tetrabodies etc. Other examples include a diabody, triabody, tetrabody, bibodies and tribodies (see for example Holliger and Hudson, 2005, Nature Biotech 23(9): 1 126-1136; Schoonjans et al. 2001, Biomolecular Engineering, 17 (6), 193-202); tandem scFv, tandem scFv-Fc, FabFv, Fab'Fv, FabdsFv, Fab-scFv, Fab'-scFv, diFab, diFab', scdiabody, scdiabody-Fc, ScFv-Fc-scFv, scdiabody-CH3, IgG-scFv, scFv-IgG, V-IgG, IgG-V, DVD-Ig, DuoBody, Fab-Fv-Fv, Fab-Fv-Fc and Fab-dsFv-PEG fragments described in WO2009040562, WO2010035012, WO2011/08609, WO2011/030107 and WO201 1/061492, respectively.

Furthermore, the antibody of the invention may comprise along with the antigen-binding portions binding HVEM and CD9, also at least an additional antigen-binding portion. Therefore, in one embodiment, there is provided an antibody, preferably a monoclonal antibody, comprising a first antigen-binding portion binding HVEM and a second antigen-binding portion binding CD9, wherein the antibody is humanised and wherein the antibody further comprises an additional antigen-binding portion. More preferably this antibody is capable of activating T-cells and/or enhancing induction of T-cell proliferation. The stimulation may be SEB stimulation wherein activating T-cells may result in an upregulation of CD137, CD71 and CD25.

In one embodiment, the additional antigen-binding portion is capable of increasing, i.e. extending, the half-life of the antibody. Preferably, the additional antigen-binding portion binds albumin, more preferably human serum albumin.

In one preferred embodiment, the antibody comprises a first antigen-binding portion binding the HVEM and a second antigen-binding portion binding an extracellular domain region of human CD9, wherein the extracellular domain region of CD9 is preferably loop 2 of CD9, and wherein more preferably the second antigen-binding portion binds within amino acids 112 to 195 of SEQ ID NO: 2, wherein the first and the second antigen-binding portions are located on the same antibody, i.e. they are part of the same polypeptide chain, associate via one or more non-covalent and/or covalent associations or linked so as to form one single molecule.

In another embodiment, the first antigen-binding portion binding HVEM of the antibody of the present invention comprises a first heavy chain variable region and a first light chain variable region and the second antigen-binding portion binding CD9 comprises a second heavy chain variable region and a second light chain variable region and wherein:

a. The first heavy chain variable region comprises a CDR-H1 comprising SEQ ID NO: 3, a CDR-H2 comprising SEQ ID NO: 4 and a CDR-H3 comprising SEQ ID NO: 5; and
b. The first light chain variable region comprises a CDR-L1 comprising SEQ ID NO: 6, a CDR-L2 comprising SEQ ID NO: 7 and a CDR-L3 comprising SEQ ID NO: 8; and
c. The second heavy chain variable region comprises a CDR-H1 comprising SEQ ID NO: 9, a CDR-H2 comprising SEQ ID NO: 10 and a CDR-H3 comprising SEQ ID NO: 11; and
d. The second light chain variable region comprises a CDR-L1 comprising SEQ ID NO: 12, a CDR-L2 comprising SEQ ID NO: 13 and a CDR-L3 comprising SEQ ID NO: 14;

or e. The first heavy chain variable region comprises SEQ ID NO: 15 and the first light chain variable region comprises SEQ ID NO: 17; and the second heavy chain variable region comprises SEQ ID NO: 19 and second light chain variable region comprises SEQ ID NO: 21;

or f. The first heavy chain variable region is encoded by a nucleotide sequence comprising SEQ ID NO: 16 and the first light chain variable region is encoded by a nucleotide sequence comprising SEQ ID NO: 18; and the second heavy chain variable region is encoded by a nucleotide sequence comprising SEQ ID NO: 20 and second light chain variable region is encoded by a nucleotide sequence comprising SEQ ID NO: 22.

In one embodiment, the antibody according to the present invention is prepared according to the disclosure of WO2015/181282, WO2016/009030, WO2016/009029, WO2017/093402, WO2017/093404 and WO2017/093406, which are all incorporated herein by reference.

More specifically, the antibody is made by the heterodimerization of a Fab-X and a Fab-Y.

Fab-X comprises a Fab fragment which comprises the first antigen-binding portion binding HVEM which comprises a first heavy chain variable region and a first light chain variable region wherein the first heavy chain variable region comprises a CDR-H1 comprising SEQ ID NO: 3, a CDR-H2 comprising SEQ ID NO: 4 and a CDR-H3 comprising SEQ ID NO: 5; and the first light chain variable region comprises a CDR-L1 comprising SEQ ID NO: 6, a CDR-L2 comprising SEQ ID NO: 7 and a CDR-L3 comprising SEQ ID NO: 8. The Fab comprising the first antigen-binding portion binding HVEM is linked to a scFv (clone 52SR4), preferably via a peptide linker to the C-terminal of the CH1 domain of the Fab fragment and the VL domain of the scFv. The scFv may itself also contains a peptide linker located in between its VL and VH domains.

Fab-Y also comprises a Fab fragment which comprises the second antigen-binding portion binding CD9 which comprises a second heavy chain variable region and a second light chain variable region and wherein the second heavy chain variable region comprises a CDR-H1 comprising SEQ ID NO: 9, a CDR-H2 comprising SEQ ID NO: 10 and a CDR-H3 comprising SEQ ID NO: 11; and the second light chain variable region comprises a CDR-L1 comprising SEQ ID NO: 12, a CDR-L2 comprising SEQ ID NO: 13 and a CDR-L3 comprising SEQ ID NO: 14. The Fab comprising the second antigen-binding portion binding CD9 is linked to a peptide GCN4 (clone 7P14P), preferably via a peptide linker to the CH1 domain of the Fab fragment.

The scFv of Fab-X is specific for and complementary to the peptide GCN4 of Fab-Y. As a result, when the Fab-X and the Fab-Y are brought into contact with each other, a non-covalent binding interaction between the scFv and GCN4 peptide occurs, thereby physically retaining the two antigen-binding portions in the form of a complex resulting in an antibody comprising two antigen-binding portions on the same molecule (FIG. 1).

In another embodiment, the Fab-X comprises the first antigen-binding portion binding HVEM which comprises a first heavy chain variable region comprising SEQ ID NO: 15 and the first light chain variable region comprising SEQ ID NO: 17; and Fab-Y comprises the second antigen-binding portion binding CD9 which comprises the second heavy chain variable region comprising SEQ ID NO: 19 and second light chain variable region comprising SEQ ID NO: 21.

Binding specificities may be exchanged between Fab-X and Fab-Y, i.e. in one embodiment Fab-X may comprise the antigen-binding portion binding to HVEM and Fab-Y the antigen-binding portion binding to CD9; in another embodiment Fab-X may comprise the antigen-binding portion binding to CD9 and Fab-Y the antigen-binding portion binding to HVEM.

The antibody of the present invention may be comprised in a pharmaceutical composition along with one or more pharmaceutically acceptable excipients. By pharmaceutical composition is intended a composition for both therapeutic and diagnostic use. In another aspect, the present invention provides for a pharmaceutical composition comprising an antibody, preferably a monoclonal antibody, comprising a first antigen-binding portion binding HVEM and a second antigen-binding portion binding CD9, wherein the antibody is preferably humanised and wherein the composition comprises one or more pharmaceutically acceptable excipients.

Pharmaceutically acceptable excipients in therapeutic compositions may additionally contain liquids such as water, saline, glycerol and ethanol. Additionally, auxiliary substances, such as wetting or emulsifying agents or pH buffering substances, may be present in such compositions. Such excipients enable the pharmaceutical compositions to be formulated as tablets, pills, dragees, capsules, liquids, gels, syrups, slurries and suspensions, for ingestion by the patient.

The antibody of the present invention and the pharmaceutical composition comprising such antibody may be used in therapy.

Therefore, in another aspect, the present invention provides for an antibody, preferably a monoclonal antibody, or a pharmaceutical composition comprising the antibody, and one or more pharmaceutically acceptable excipients, wherein the antibody comprises a first antigen-binding portion binding HVEM and a second antigen-binding portion binding CD9, wherein the antibody is preferably humanised and is for use in therapy.

In one embodiment of this further aspect, the antibody or composition comprising such antibody for use in therapy is an antibody comprising a first antigen-binding portion binding HVEM and a second antigen-binding portion binding an extracellular domain region of human CD9, wherein the extracellular domain region of CD9 is preferably loop 2 of CD9, and wherein more preferably the second antigen-binding portion binds within amino acids 112 to 195 of SEQ ID NO: 2, wherein the first and the second antigen-binding portions are located on the same antibody, i.e. they are part of the same polypeptide chain, associate via one or more non-covalent and/or covalent associations or linked so as to form one single molecule.

In another aspect, the present invention provides for an antibody, preferably a monoclonal antibody, or a pharmaceutical composition comprising the antibody, and one or more pharmaceutically acceptable excipients, wherein the antibody comprises a first antigen-binding portion binding HVEM and a second antigen-binding portion binding CD9, wherein the antibody is preferably humanised and is for use in the treatment of cancer and/or an infectious disease.

In another embodiment, the antibody or composition comprising such antibody for use in the treatment of cancer and/or an infectious disease is an antibody comprising a first antigen-binding portion binding HVEM and a second antigen-binding portion binding an extracellular domain region of human CD9, wherein the extracellular domain region of CD9 is preferably loop 2 of CD9, and wherein more preferably the second antigen-binding portion binds within amino acids 112 to 195 of SEQ ID NO: 2, wherein the first and the second antigen-binding portions are located on the same antibody, i.e. they are part of the same polypeptide chain, associate via one or more non-covalent and/or covalent associations or linked so as to form one single molecule.

In yet another aspect, the present invention provides for a method for treating a subject afflicted with cancer and/or an infectious disease, comprising administering to the subject a pharmaceutically effective amount of an antibody, preferably a monoclonal antibody, or a pharmaceutical composition comprising the antibody, and one or more pharmaceutically acceptable excipients, wherein the antibody comprises a first antigen-binding portion binding HVEM and a second antigen-binding portion binding CD9, wherein the antibody is preferably humanised.

The subjects to be treated is preferably a human subject. In one embodiment, there is provided for a method for treating a human subject afflicted with cancer and/or an infectious disease, comprising administering to the subject a pharmaceutically effective amount of an antibody, preferably a monoclonal antibody, or a pharmaceutical composition comprising the antibody and one or more pharmaceutically acceptable excipients, wherein the antibody comprises a first antigen-binding portion binding HVEM and a second antigen-binding portion binding CD9, wherein the antibody is preferably humanised.

In yet another embodiment, the method for treating a human subject afflicted with cancer and/or an infectious disease comprises administering an antibody or composition comprising such antibody comprising a first antigen-binding portion binding HVEM and a second antigen-binding portion binding an extracellular domain region of human CD9, wherein the extracellular domain region of CD9 is preferably loop 2 of CD9, and wherein more preferably the second antigen-binding portion binds within amino acids 112 to 195 of SEQ ID NO: 2, wherein the first and the second antigen-binding portions are located on the same antibody, i.e. they are part of the same polypeptide chain, associate via one or more non-covalent and/or covalent associations or linked so as to form one single molecule.

In another aspect of the present invention, there is provided the use of an antibody, preferably a monoclonal antibody, or a pharmaceutical composition comprising the antibody, and one or more pharmaceutically acceptable excipients, wherein the antibody comprises a first antigen-binding portion binding HVEM and a second antigen-binding portion binding CD9, wherein the antibody is preferably humanised, in the manufacture of a medicament for treating cancer and/or an infectious disease.

Example of cancers that may be treated using the antibody, or pharmaceutical composition comprising such antibody, include but are not limited to, Acute Lymphoblastic Leukaemia, Acute Myeloid Leukaemia, Adrenocortical Carcinoma, AIDS-Related Cancers Kaposi Sarcoma (Soft Tissue Sarcoma), AIDS-Related Lymphoma, Primary CNS Lymphoma, Anal Cancer, Appendix Cancer Astrocytomas, Atypical Teratoid/Rhabdoid Tumour, Brain Cancer, Basal Cell Carcinoma of the Skin, Bile Duct Cancer, Bladder Cancer, Bone Cancer (includes Ewing Sarcoma and Osteosarcoma and Malignant Fibrous Histiocytoma), Breast Cancer, Bronchial Tumours, Burkitt Lymphoma, Carcinoid Tumour, Cardiac (Heart) Tumours, Embryonal Tumours, Germ Cell Tumour, Primary CNS Lymphoma, Cervical Cancer, Cholangiocarcinoma, Chordoma, Chronic Lymphocytic Leukaemia, Chronic Myelogenous Leukaemia, Chronic Myeloproliferative Neoplasms, Colorectal Cancer, Craniopharyngioma, Cutaneous T-Cell Lymphoma, Ductal Carcinoma In Situ, Endometrial Cancer (Uterine Cancer), Ependymoma, Oesophageal Cancer, Esthesioneuroblastoma (Head and Neck Cancer), Ewing Sarcoma (Bone Cancer), Extracranial Germ Cell Tumour, Extragonadal Germ Cell Tumour, Eye Cancer, Intraocular Melanoma, Retinoblastoma, Fallopian Tube Cancer, Fibrous Histiocytoma of Bone, Malignant, and Osteosarcoma, Gallbladder Cancer, Gastric (Stomach) Cancer, Gastrointestinal Carcinoid Tumour, Gastrointestinal Stromal Tumours (Soft Tissue Sarcoma), Ovarian Germ Cell Tumours, Testicular Cancer, Gestational Trophoblastic Disease, Hairy Cell Leukaemia, Head and Neck Cancer, Hepatocellular (Liver) Cancer, Histiocytosis, Langerhans Cell Hodgkin Lymphoma, Hypopharyngeal Cancer, Intraocular Melanoma, Isle T-cell Tumours, Pancreatic Neuroendocrine Tumours, Kaposi Sarcoma (Soft Tissue Sarcoma), Kidney (Renal Cell) Cancer, Langerhans Cell Histiocytosis, Laryngeal Cancer, Leukaemia, Lip and Oral Cavity Cancer, Liver Cancer, Lung Cancer (Non-Small Cell and Small Cell), Male Breast Cancer, Malignant Fibrous Histiocytoma of Bone and Osteosarcoma, Melanoma, Intraocular (Eye) Childhood Intraocular, Merkel Cell Carcinoma, Mesothelioma, Metastatic Cancer, Metastatic Squamous Neck Cancer with Occult Primary, Midline Tract Carcinoma With NUT Gene Changes, Mouth Cancer, Multiple Endocrine Neoplasia Syndromes, Multiple Myeloma/Plasma Cell Neoplasms, Mycosis Fungoides (Lymphoma), Myelodysplastic Syndromes, Myelodysplastic/Myeloproliferative Neoplasms, Myelogenous Leukaemia, Chronic, Myeloid Leukaemia, Acute, Myeloproliferative Neoplasms, Nasal Cavity and Paranasal Sinus Cancer, Nasopharyngeal Cancer, Neuroblastoma, Non-Hodgkin Lymphoma, Non-Small Cell Lung Cancer, Oral Cancer, Lip and Oral Cavity Cancer and Oropharyngeal Cancer, Osteosarcoma and Malignant Fibrous Histiocytoma of Bone, Ovarian Cancer, Pancreatic Cancer, Pancreatic Neuroendocrine Tumours (Isle T-cell Tumours), Papillomatosis, Paraganglioma, Paranasal Sinus and Nasal Cavity Cancer, Parathyroid Cancer, Penile Cancer, Pharyngeal Cancer, Pheochromocytoma, Pituitary Tumour, Plasma Cell Neoplasm/Multiple Myeloma, Pleuropulmonary Blastoma, Pregnancy and Breast Cancer, Primary Central Nervous System (CNS) Lymphoma, Primary Peritoneal Cancer, Prostate Cancer, Rectal Cancer, Recurrent Cancer, Renal Cell (Kidney) Cancer, Retinoblastoma, Rhabdomyosarcoma, Salivary Gland Cancer, Sarcoma Childhood Rhabdomyosarcoma, Childhood Vascular Tumours, Ewing Sarcoma, Kaposi Sarcoma, Osteosarcoma, Soft Tissue Sarcoma, Uterine Sarcoma, Sezary Syndrome, Skin Cancer, Small Intestine Cancer, Squamous Cell Carcinoma of the Skin, Squamous Neck Cancer with Occult Primary, Stomach (Gastric) Cancer, Cutaneous T-Cell Lymphoma, Testicular Cancer, Throat Cancer, Nasopharyngeal Cancer, Oropharyngeal Cancer, Hypopharyngeal Cancer, Thymoma and Thymic Carcinoma, Thyroid Cancer, Transitional Cell Cancer of the Renal Pelvis and Ureter, Urethral Cancer, Uterine Cancer, Endometrial Uterine Sarcoma, Vaginal Cancer, Vascular Tumours, Vulvar Cancer and Wilms Tumour, and any combinations of said cancers. The present invention is also applicable to treatment of metastatic cancers.

The antibody according to the present invention, or the pharmaceutical composition comprising such antibody, may be administered concomitantly or sequentially to one or more additional cancer therapies. By cancer therapies is intended drug-based therapies as well as other type of cancer therapies such as radiotherapies.

The invention will now be further described by way of examples with references to embodiments illustrated in the accompanying drawings

EXAMPLES

Example 1: T-Cell Activation Primary Screen

The activation status of T-cells can be assessed through their expression of cell surface markers and secreted cytokines which play important roles in cellular function. Activated T-cells for example upregulate CD25, CD71 and CD137 on their surface. T-cells in the tumour microenvironment are often maintained in a suppressed state and express only low levels of these proteins. Agents that overcome this suppression and induce T-cell activation and proliferation have tremendous therapeutic potential as they may unleash effective anti-tumour T-cell responses and promote cancer elimination.

To identify novel modulators of T-cell activation, a large screen was undertaken whereby 49 antigen specificities were combined to generate a grid of bispecific antibodies with a theoretical size of 1,176 possible bispecific combinations. The specificities were selected from the literature as being expressed on T-cells or expressed on other cell types involved in interactions with T-cells. Of this potential grid, 969 novel antigen bispecific constructs were tested, covering 82.4% of the possible combinations. Between 1 and 4 different antibodies were tested for each specificity, and all were tested on peripheral blood mononuclear cells (PBMC) from donors in combination with a negative control arm to identify the effect of the monovalent forms of the construct.

PBMC represent the major leukocyte classes involved in both innate and adaptive immunity, apart from granulocytes. PBMC comprise a heterogenous population of cells which when manipulated in vitro provide a relatively more relevant physiological environment compared to isolated component cell types such as T-cell types such as T-cells and monocytes, that are no longer capable of responding to paracrine and autocrine signals provided by other cells. As such identification of molecules modulating specific subsets of cells within the wider PBMC population, have increased translational potential to more complex biological systems, ultimately increasing success rates for modulating immune cell interactions in disease.

Each bispecific combination was tested on two PBMC donors. The negative control arm is a Fab from an antibody raised to an antigen not expressed on PBMC.

Fusion proteins were prepared according to the disclosure of WO2015/181282, WO2016/009030, WO2016/009029, WO2017/093402, WO2017/093404 and WO2017/093406, which are all incorporated herein by reference. The first fusion protein (A-X) includes a Fab fragment (A of the A-X) with specificity to one antigen, which is linked to X, a scFv (clone 52SR4) via a peptide linker to the C-terminal of the CH1 domain of the Fab fragment and the VL domain of the scFv. The scFv itself also contains a peptide linker located in between its VL and VH domains.

The second fusion protein (B-Y) includes a Fab fragment (B of the B-Y) with specificity to another antigen. However, in comparison to the first protein, the Fab fragment B is attached to Y, a peptide GCN4 (clone 7P14P) via a peptide linker to the CH1 domain of the Fab fragment.

Figure 2:
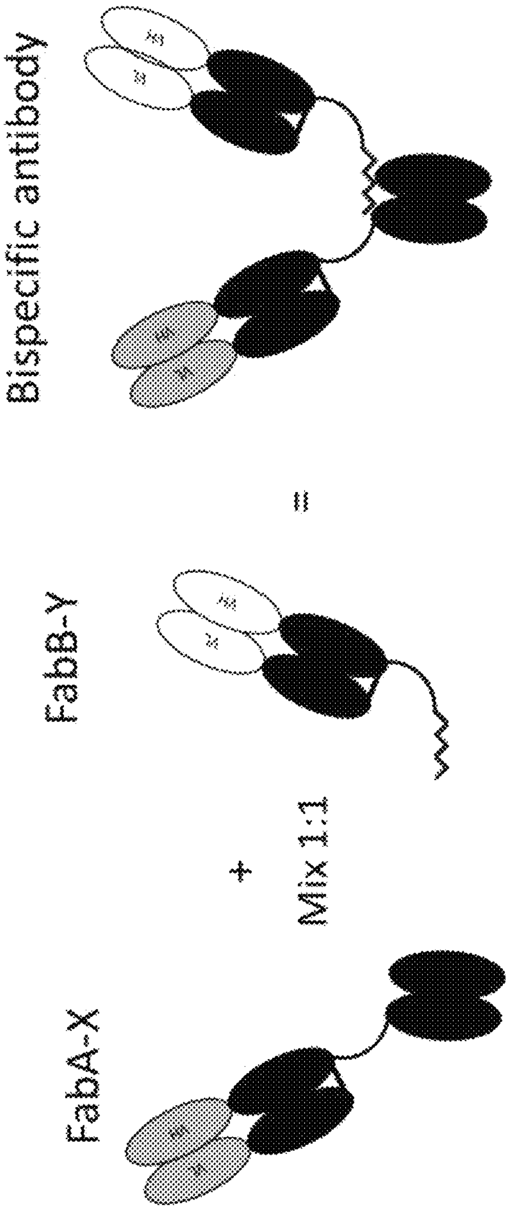
FIG. 2. General representation of a Fab-X and Fab-Y comprising antigen-binding portions and of the resulting bispecific antibody FIG. 3. Log 2 fold change in the median fluorescence intensity (MFI) of CD25 expression on CD4+ T-cells in the presence of *Staphylococcus Aureus* Enterotoxin B (SEB) (1 μg/mL) stimulation. PBMC cultures were treated with 1 μg/mL for 48 hours in the presence of either the HVEM-CD9 bispecific antibodies or control antibodies followed by flow cytometry for identifying the CD4+ T-cell population. Log 2 fold changes were calculated for the MFI of CD25 levels in the treated samples relative to the SEB stimulated controls. N=4 donors, 2 technical replicates ±standard error of the mean (SEM).

The scFv, X, is specific for and complementary to the peptide GCN4, Y. As a result, when the two fusion proteins are brought into contact with each other, a non-covalent binding interaction between the scFv and GCN4 peptide occurs, thereby physically retaining the two fusion proteins in the form of a complex mimicking an antibody comprising two different antigen-binding portions on the same molecule (FIG. 2).

Purified Fab-X and Fab-Y with varying specificities were incubated together for 60 minutes (in a 37° C./5% $CO_2$ environment) at an equimolar concentration. The final molarity of each tested complex was 100 nM. In 384-well tissue culture plates, 1.0E+05 PBMC were added to wells, to which were added pre-formed Fab-X/Fab-Y bispecific antibodies. Following addition of the bispecific antibodies, the cells were incubated for 48 hours at 37° C./5% $CO_2$, with or without 1 μg/mL (final concentration) *Staphylococcal* Enterotoxin-B (SEB) superantigen. After 48 hours the plates were centrifuged at 500×g for 5 minutes at 4° C. Cell culture conditioned media was transferred from the cell pellets to fresh plates and frozen at −80° C. Cells were washed with 60 μL FACS buffer two times by centrifugation, followed by resuspension of the pellets by shaking the plates at 2200 rpm for 30 seconds. The cells were stained with a panel of fluorescently labelled antibodies as listed in the Table 2 and incubated at 4° C. in the dark for 1 hour.

TABLE 2

| Epitope | Fluorophore | Clone | Source | Dilution |
|---|---|---|---|---|
| CD56 | APC | HCD56 | BioLegend ® | 40 |
| CD14 | PE/Cy7 | M5E2 | BD Pharmagen ® | 80 |
| CD8 | BV650 | RPA-T8 | BioLegend ® | 80 |
| CD4 | BV605 | RPA-T4 | BD Horizon ® | 40 |
| CD19 | PE-Cy5 | HIB19 | BD Pharmagen ® | 20 |
| CD45RO | BV786 | UCHL1 | BD Horizon ® | 40 |
| CD71 | FITC | M-A712 | BD Pharmagen ® | 20 |
| CD25 | BV510 | M-A251 | BD Horizon ® | 40 |
| CD137 | PE | 4B4-1 | BD Pharmagen ® | 20 |
| Live/Dead | Near IR | | Thermo Scientific ® | 1000 |

After this time, cells were washed twice with FACS buffer, before fixing with 2% paraformaldehyde (BD CellFix™, diluted in $dH_2O$) and stored overnight at 4° C. The plates were centrifuged at 500×g for 5 minutes, the fixation buffer aspirated to waste and the cells resuspended in a residual volume of 10 μL for acquisition on the iQue® Screener Plus (IntelliCyt®). The data analysis software package ForeCyt™ (IntelliCyt®) was used to gate on CD14+ monocytes, CD56+ NK cells, CD19+ B-cells, CD4+ and CD8+ memory and naïve T-cells. For each cell population the cellular expression of CD25 and CD71 was measured as reported median fluorescent intensity values. The data were then used to calculate the log 2 fold changes of expression relative to control well values.

The resulting flow cytometry data were analysed by identification of the CD4+ and CD8+ memory and naïve T-cells and well as the B cells, NK cells and monocytes. The MFI values of the 3 activation markers CD71, CD137 and CD25 were then determined and the log 2 fold changes calculated relative to the control wells for each cell population. These results were deposited into the visualisation software Spotfire®, where it was possible to identify antigen pairs capable of inducing an increase in T-cell activation.

When considering antigen pairs capable of upregulating the activation markers CD25, CD137 and CD71 on T-cells in the presence of an SEB stimulation, but not in unstimulated conditions, the HVEM-CD9 bispecific pair was identified.

The HVEM-CD9 bispecific antibody was therefore taken into subsequent assays to show that its effect was reproducible across a larger number of donors.

Example 2: HVEM-CD9 Follow Up Assay

To confirm the effect of HVEM-CD9 on stimulation of T-cells, a further 4 PBMC donors were assayed in SEB-stimulated and unstimulated conditions.

A grid of fusion proteins Fab-X and Fab-Y were created by diluting equimolar (1 μM) quantities of Fab-X (Fab-scFv) and Fab-Y (Fab-peptide) with specificity for HVEM and CD9 in TexMACS™ media (Miltenyi Biotec®) containing 100 U/mL penicillin/100 μg/mL streptomycin. Mixtures of equimolar (1 μM) Fab-Y proteins were also generated in the same manner. The Fab-X and Fab-Y fusion proteins were incubated together for 1 hour (in a 37° C./5% $CO_2$ environment), at a final concentration of 500 nM. Negative control wells containing TexMACS™ media only were also generated alongside the Fab-X and Fab-Y wells.

During this time, cryopreserved human PBMCs isolated from platelet leukapheresis cones were thawed and washed in TexMACS™ media and resuspended at $3.33\times10^6$ cells/mL. The PBMCs were then seeded into 384 well flat bottom tissue culture plates (Greiner Bio-One®) at 30 μl/well ($1\times10^5$ PBMCs).

A total of 10 μl of Fab-X and Fab-Y complexes were transferred to the plates containing 30 μl PBMCs. The PBMCs were then either left unstimulated by the addition of 10 μl of TexMACS™ media, or stimulated with 10 μl of SEB (1 μg/mL final concentration). This resulted in a final assay concentration of Fab-X and Fab-Y complexes of 100 nM. The plates were then returned to a 37° C./5% $CO_2$ environment for 48 hours.

After 48 hours the plates were centrifuged at 500×g for 5 minutes at 4° C. Conditioned medium was transferred from the cell pellets to fresh plates and frozen at −80° C. Cells were washed with 60 μL FACS buffer two times by centrifugation, followed by resuspension of the pellets by shaking the plates at 2200 rpm for 30 seconds. The cells were stained with a panel of fluorescently labelled antibodies as listed in Table 2 and incubated at 4° C. in the dark for 1 hour. After this time, cells were washed twice with FACS buffer, before fixing with 2% paraformaldehyde (BD CellFix™ diluted in $dH_2O$) and stored overnight at 4° C. The plates were centrifuged at 500×g for 5 minutes, the fixation buffer aspirated to waste and the cells resuspended in a residual volume of 10 μL for acquisition on the iQue® Screener Plus (IntelliCyt®).

The data analysis software package ForeCyt™ (IntelliCyt®) was used to gate on CD14+ monocytes, CD56+ NK cells, CD19+ B-cells, CD4+ and CD8+ memory and naïve T-cells. For each cell population the cellular expression of CD25, CD71 and CD137 was measured as reported median fluorescent intensity values. The data were then used to calculate the log 2 fold changes of expression relative to control well values.

Figure 3:
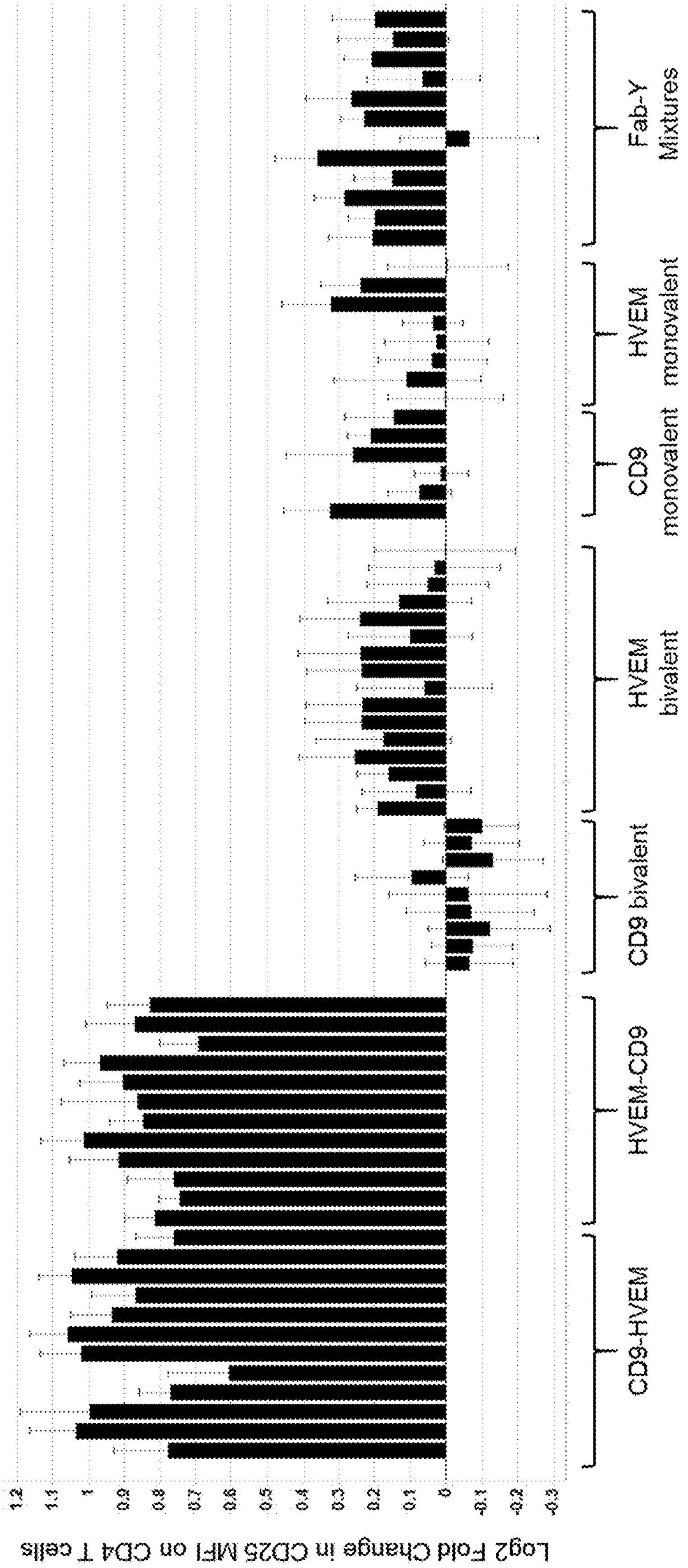
Figure 4:
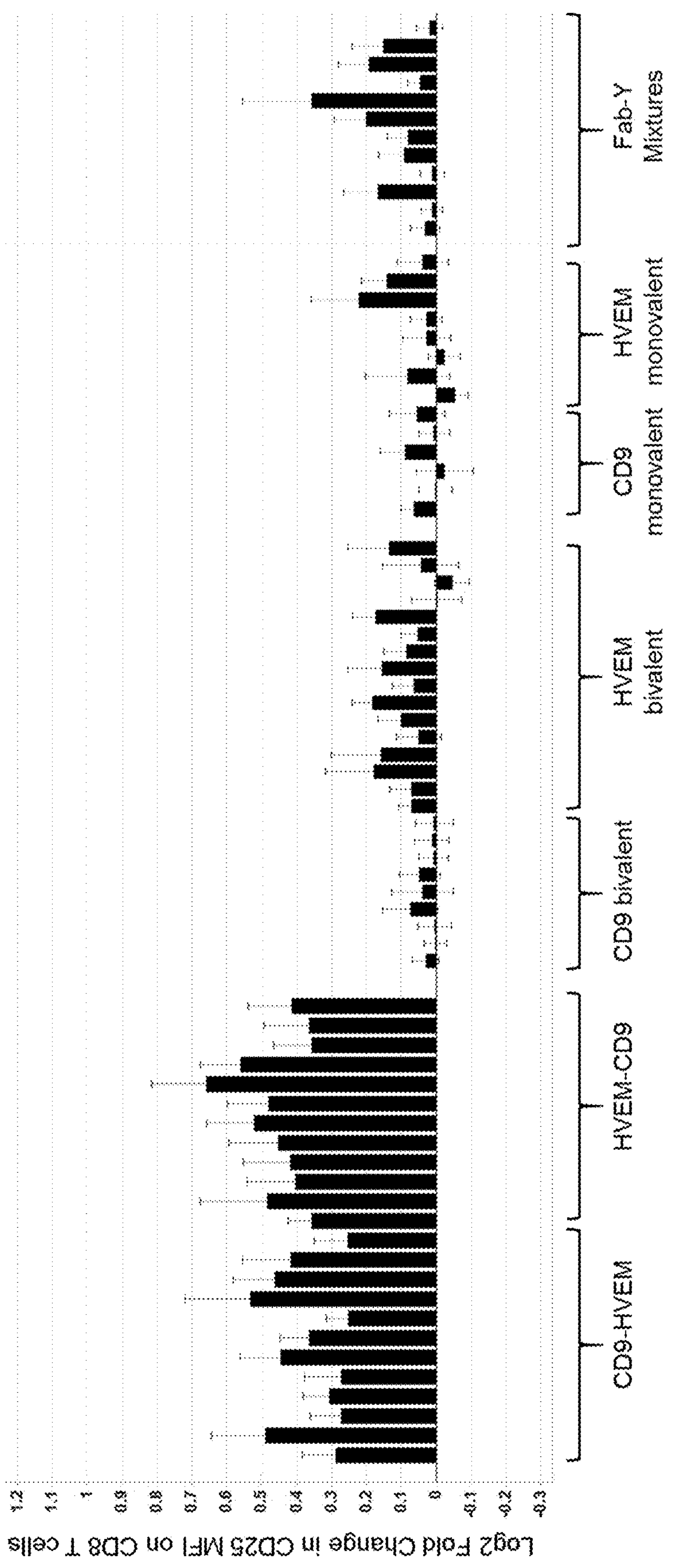
FIG. 4. Log 2 fold change in the MFI of CD25 expression on CD8+ T-cells in the presence of SEB (1 μg/mL) stimulation. PBMC cultures were treated with *Staphylococcus Aureus* Enterotoxin B (SEB) at 1 μg/mL for 48 hours in the presence of either the HVEM-CD9 bispecific antibodies or control antibodies. The samples were then analysed by flow cytometry and the CD8+ T-cell population identified. Log 2 fold changes were calculated for the MFI of CD25 levels in the treated samples relative to the SEB stimulated controls. N=4 donors, 2 technical replicates ±SEM.

Twenty-Four Fab-X/Fab-Y bispecific antibodies showed increased expression of the activation marker CD25 on CD4+ (FIG. 3) and CD8+ (FIG. 4) T-cells with SEB stimulation, while the control constructs did not lead to this increase. The bivalents (i.e. formed by a fusion where both Fabs in the Fab-X and Fab-Y are specific for CD9 or HVEM as the case may be) and monovalent antibodies for CD9 or HVEM (i.e. formed by a fusion where the Fab is specific for CD9 or HVEM but the other component Fab is a negative control) did not lead to a similar increase in the activation marker fluorescence intensity on either cell populations, suggesting that a monospecific antibody binding CD9 alone or HVEM alone, whether in a monovalent or bivalent fashion, is unable to stimulate activation in the absence of the binding to the other antigen. The small increases in CD25 expression detected by the HVEM bivalent and monovalent controls in CD4+ T-cells, however were only small increases, which could only be greatly enhanced by the co-targeting of CD9. Furthermore, the mixture of an antibody binding solely to HVEM and an antibody binding solely to CD9 (Fab-Y mixture) also had no enhanced stimulatory effect on the T-cell populations compared to the HVEM controls, implying the requirement for the antigen-binding portions binding HVEM and CD9 to be on the same chain, associated via non-covalent associations or linked for the stimulatory function to occur.

Figure 5:
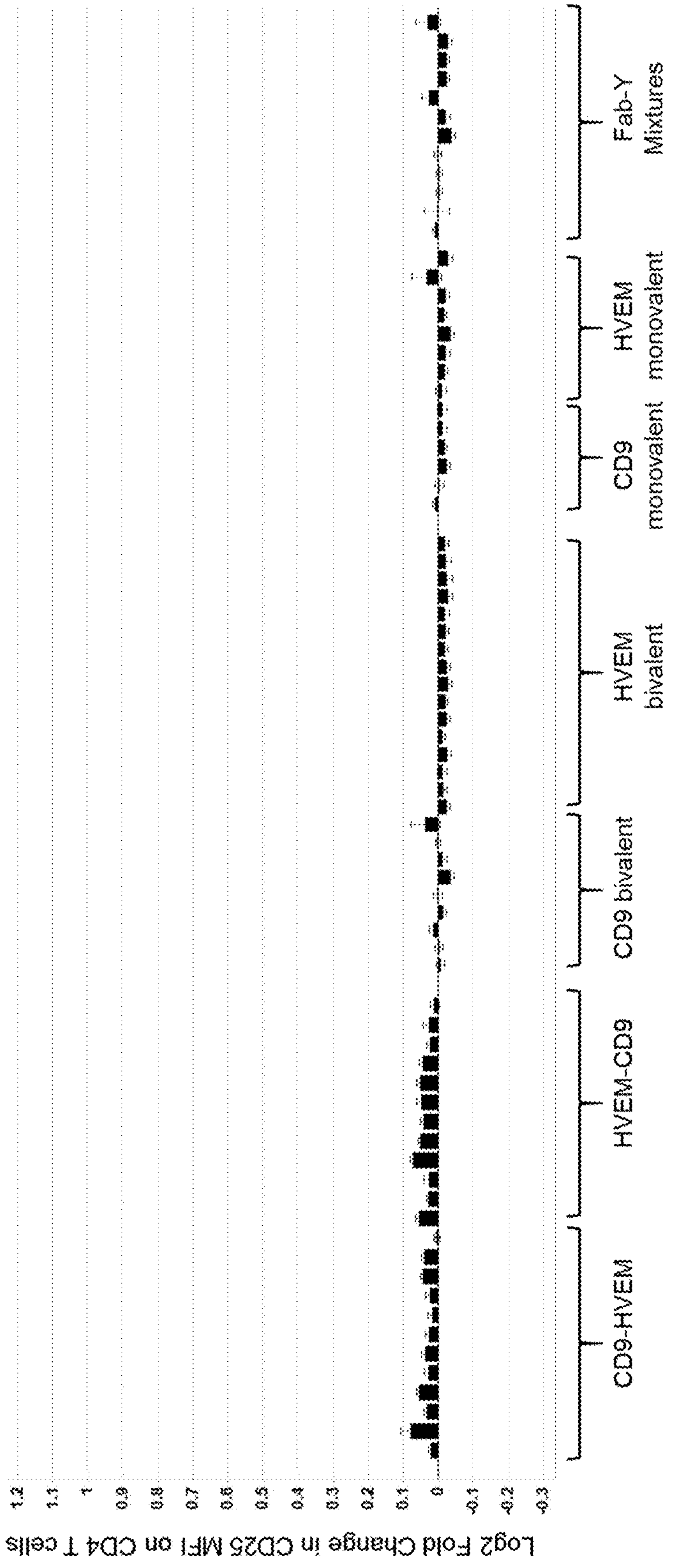
FIG. 5. Log 2 fold change in the MFI of CD25 expression on CD4+ T-cells in the absence of any stimulation. PBMC were cultured for 48 hours in the presence of either the HVEM-CD9 bispecific antibodies or control antibodies. The samples were then analysed by flow cytometry and the CD4+ T-cell population identified. Log 2 fold changes were calculated for the MFI of CD25 levels in the treated samples relative to the unstimulated controls. N=4 donors, 2 technical replicates±SEM.
Figure 6:
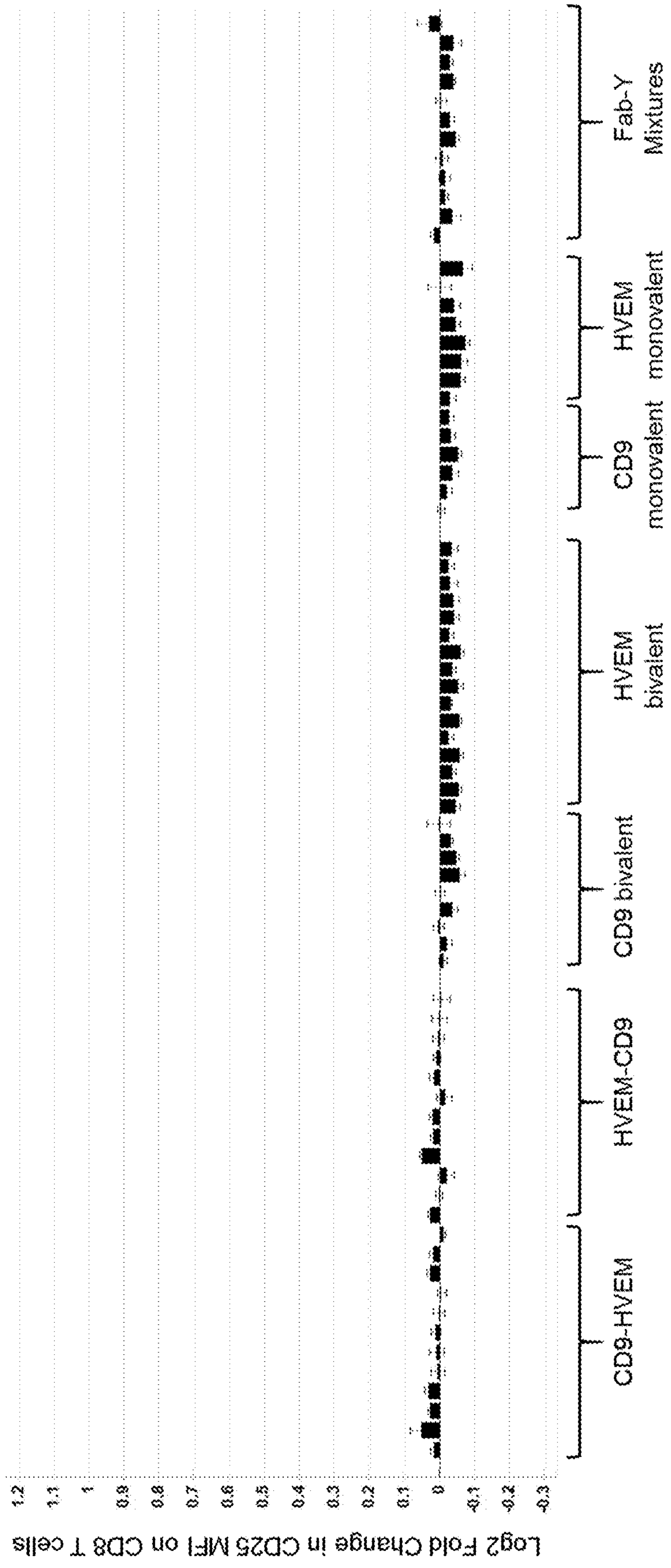
FIG. 6. Log 2 fold change in the MFI of CD25 expression on CD8+ T-cells in the absence of any stimulation. PBMC were cultured for 48 hours in the presence of either the HVEM-CD9 bispecific antibodies or control antibodies. The samples were then analysed by flow cytometry and the CD8+ T-cell population identified. Log 2 fold changes were calculated for the MFI of CD25 levels in the treated samples relative to the anti-CD3 stimulated controls. N=4 donors, 2 technical replicates ±SEM.
Figure 7:
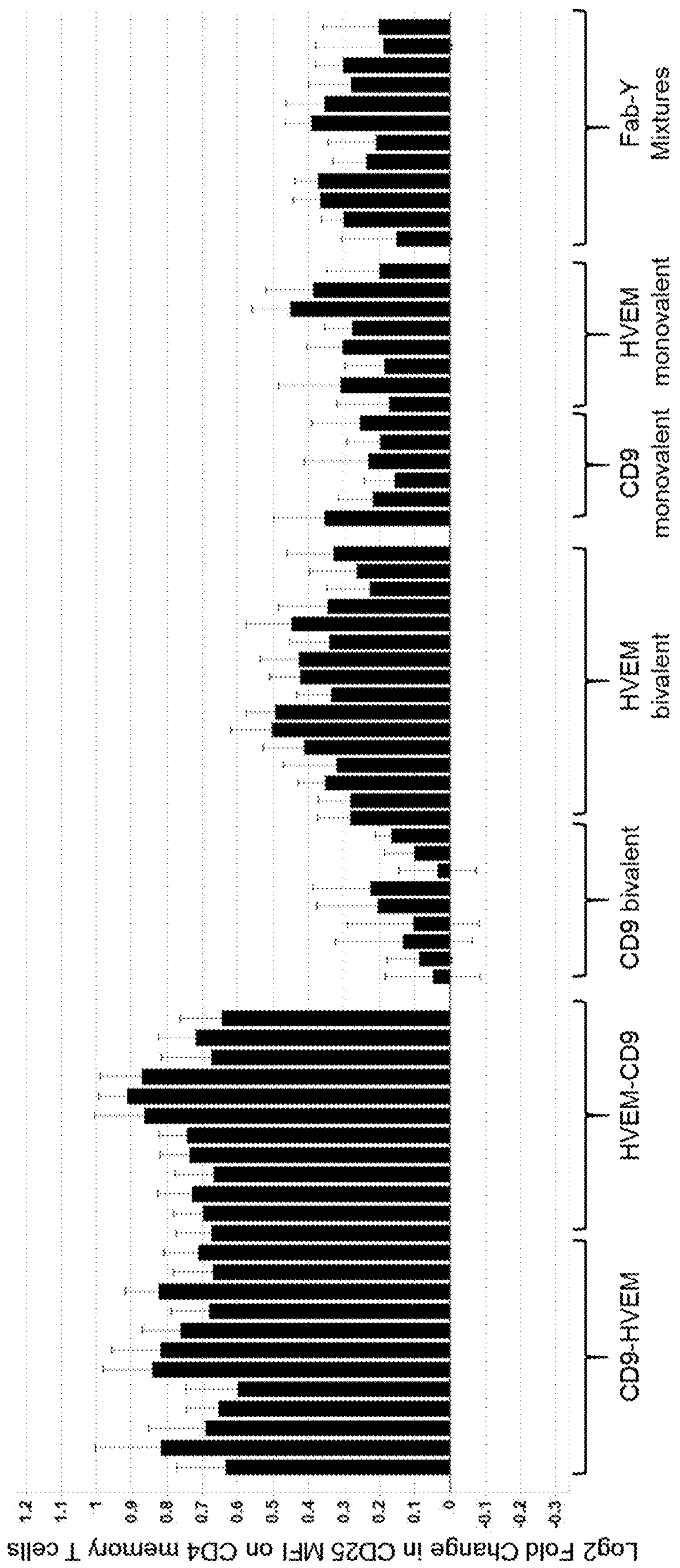
FIG. 7. Log 2 fold change in the MFI of CD25 expression on CD4+ memory T-cells in the presence of SEB (1 μg/mL) stimulation. PBMC cultures were treated with *Staphylococcus Aureus* Enterotoxin B (SEB) at 1 μg/mL for 48 hours in the presence of either the HVEM-CD9 bispecific antibodies or control antibodies. The samples were then analysed by flow cytometry and the CD4+ T-cell population identified. Log 2 fold changes were calculated for the MFI of CD25 levels in the treated samples relative to the SEB stimulated controls. N=4 donors, 2 technical replicates ±SEM.
Figure 8:
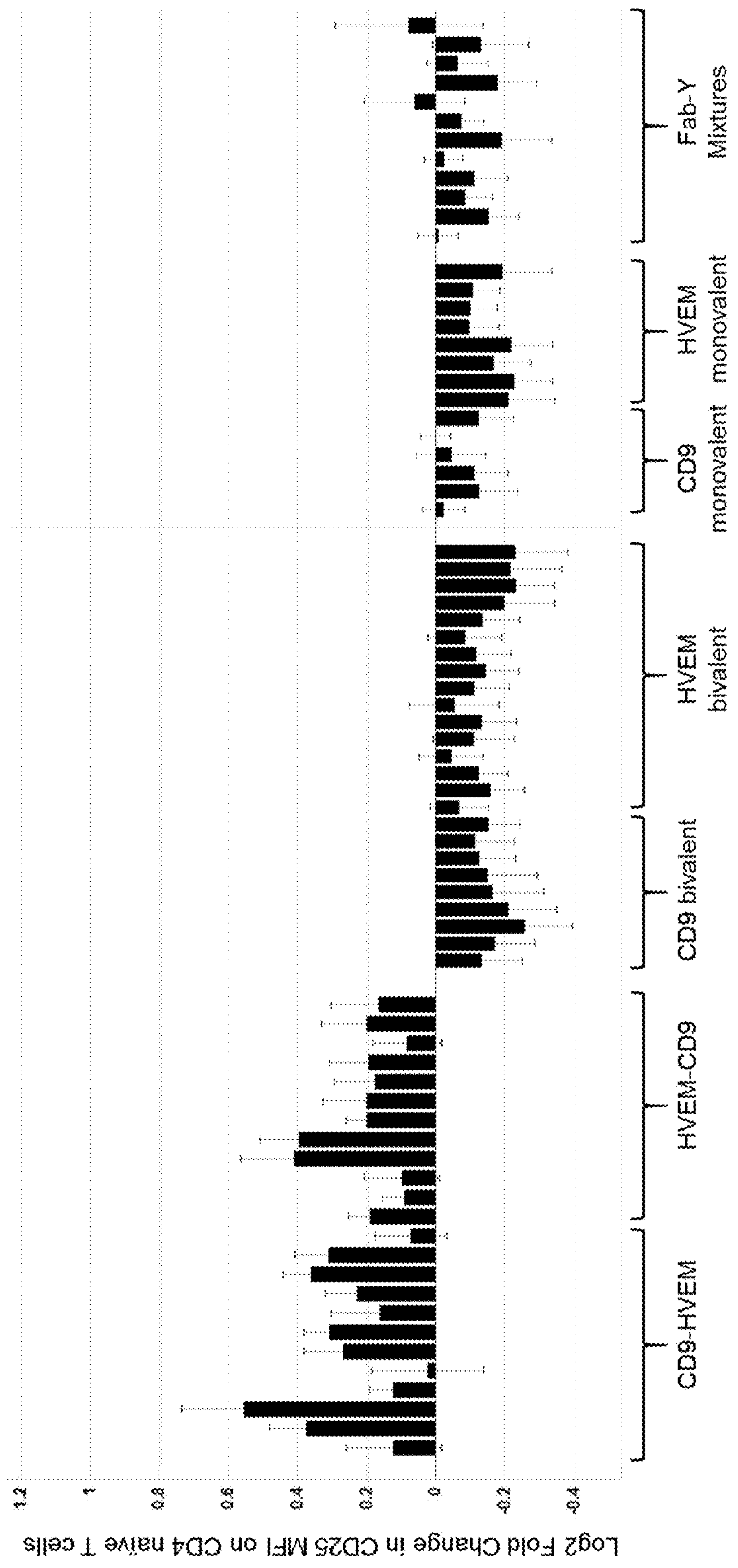
FIG. 8. Log 2 fold change in the MFI of CD25 expression on CD4+ naïve T-cells in the presence of SEB (1 μg/mL) stimulation. PBMC cultures were treated with *Staphylococcus Aureus* Enterotoxin B (SEB) at 1 μg/mL for 48 hours in the presence of either the HVEM-CD9 bispecific antibodies or control antibodies. The samples were then analysed by flow cytometry and the CD4+ T-cell population identified. Log 2 fold changes were calculated for the MFI of CD25 levels in the treated samples relative to the SEB stimulated controls. N=4 donors, 2 technical replicates ±SEM.
Figure 9:
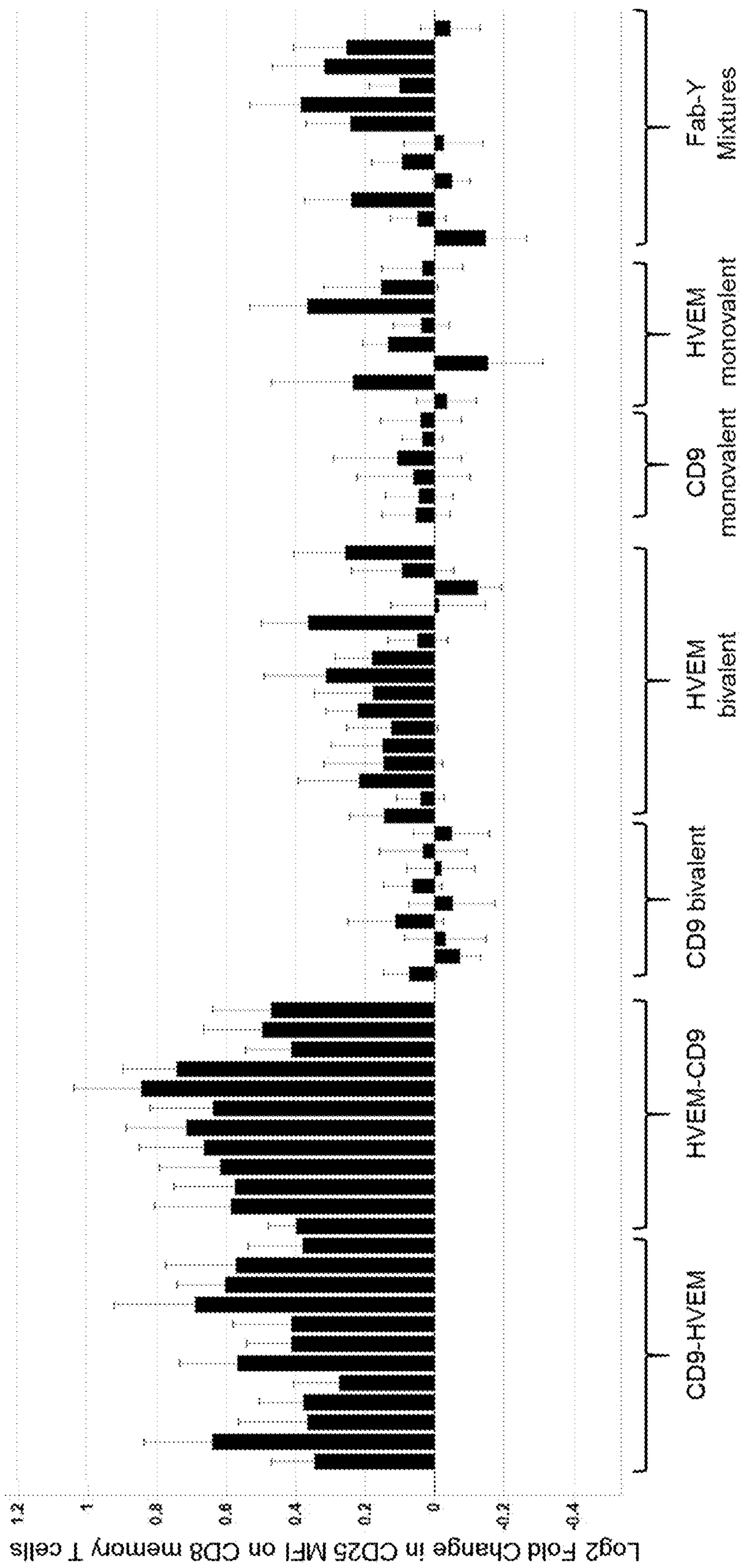
FIG. 9. Log 2 fold change in the MFI of CD25 expression on CD8+ memory T-cells in the presence of SEB (1 μg/mL) stimulation. PBMC cultures were treated with *Staphylococcus Aureus* Enterotoxin B (SEB) at 1 μg/mL for 48 hours in the presence of either the HVEM-CD9 bispecific antibodies or control antibodies. The samples were then analysed by flow cytometry and the CD8+ T-cell population identified. Log 2 fold changes were calculated for the MFI of CD25 levels in the treated samples relative to the SEB stimulated controls. N=4 donors, 2 technical replicates ±SEM.
Figure 10:
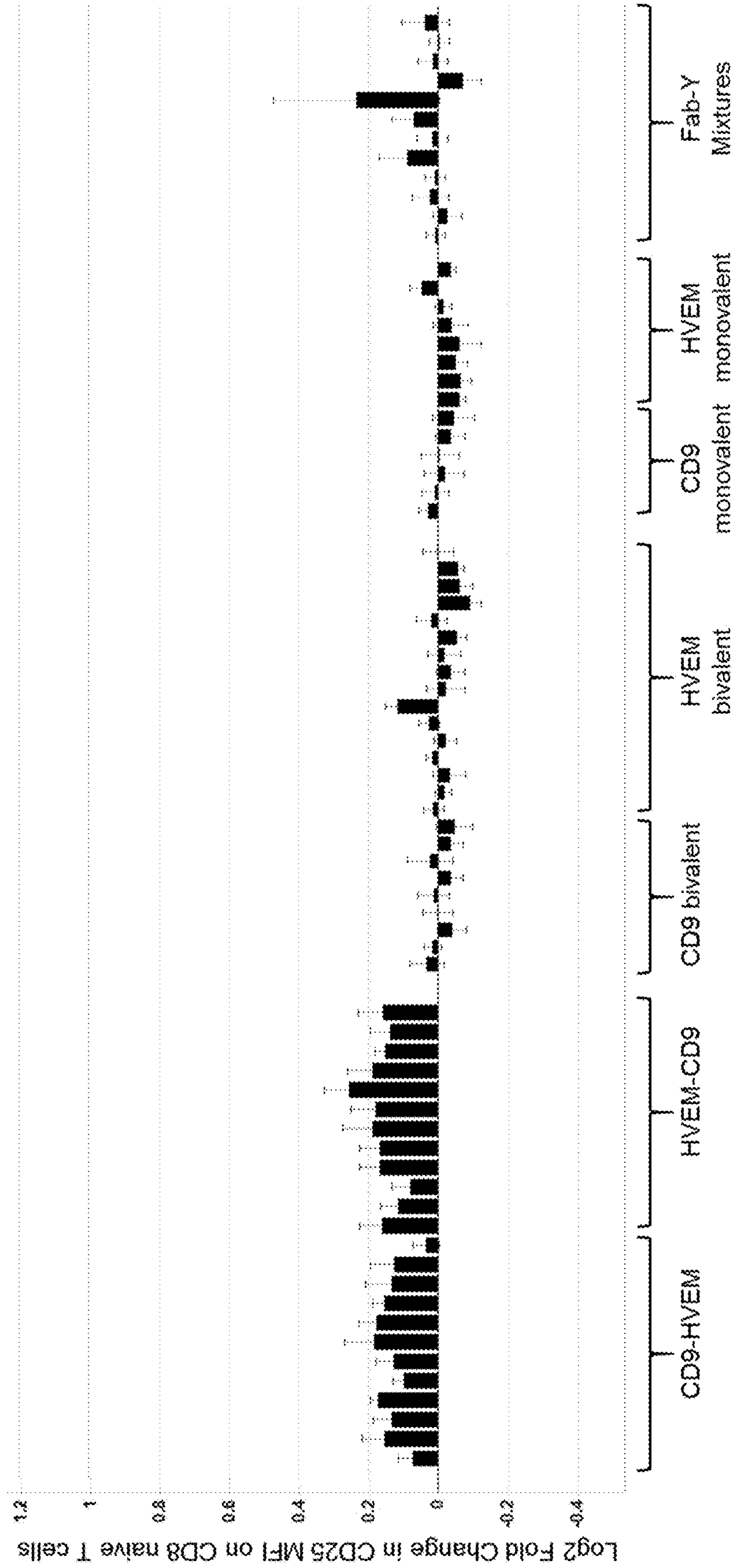
FIG. 10. Log 2 fold change in the MFI of CD25 expression on CD8+ naïve T-cells in the presence of SEB (1 μg/mL) stimulation. PBMC cultures were treated with *Staphylococcus Aureus* Enterotoxin B (SEB) at 1 μg/mL for 48 hours in the presence of either the HVEM-CD9 bispecific antibodies or control antibodies. The samples were then analysed by flow cytometry and the CD8+ T-cell population identified. Log 2 fold changes were calculated for the MFI of CD25 levels in the treated samples relative to the SEB stimulated controls. N=4 donors, 2 technical replicates ±SEM.

When studied in unstimulated conditions the HVEM/CD9 bispecific antibodies did not lead to any increases in activation marker fluorescence intensity in either CD4+ cells (FIG. 5) or CD8+ cells (FIG. 6). This confirms that the binding of both HVEM and CD9 does not lead to the unwanted activation of resting T-cells.

Furthermore, it was possible to measure the level of CD25 expression on naïve versus memory T-cell populations by the separation of the CD45RO-expressing memory cells from the CD45RO non-expressing naïve T-cell populations. Upon analysis of these sub populations a preference for upregulation of CD25 on the memory CD4+ and CD8+ T-cell populations compared to the naïve populations was identified (FIGS. 7-10). This suggests that HVEM-CD9 bispecific antibodies could preferentially target the memory T-cell populations, enhancing their therapeutic potential.

Figure 11:
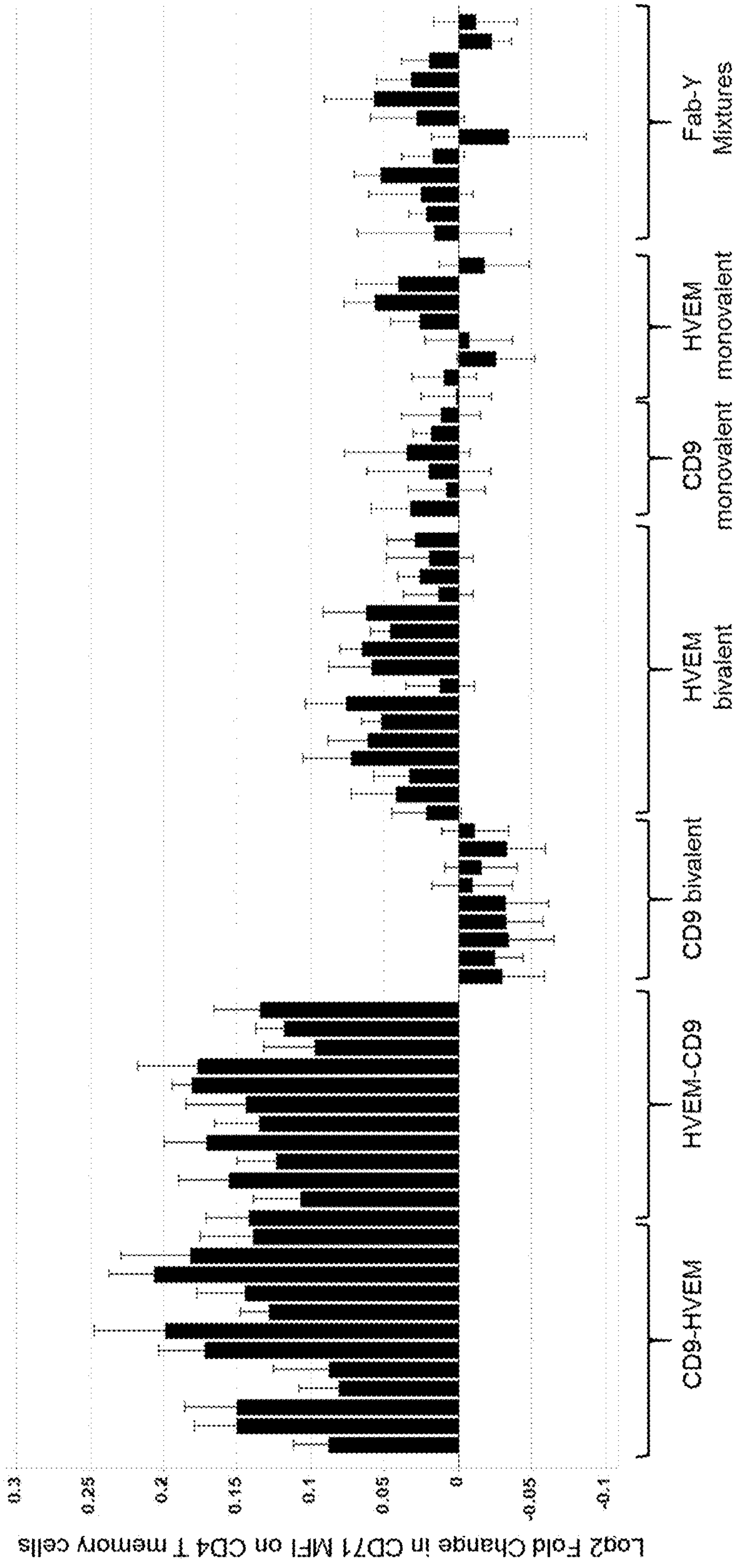
FIG. 11. Log 2 fold change in the MFI of CD71 expression on CD4+ T memory cells in the presence of SEB (1 μg/mL) stimulation. PBMC cultures were treated with *Staphylococcus Aureus* Enterotoxin B (SEB) at 1 μg/mL for 48 hours in the presence of either the HVEM-CD9 bispecific antibodies or control antibodies. The samples were then analysed by flow cytometry and the CD4+ memory T-cell population identified. Log 2 fold changes were calculated for the MFI of CD71 levels in the treated samples relative to the SEB stimulated controls. N=4 donors, 2 technical replicates ±SEM.
Figure 12:
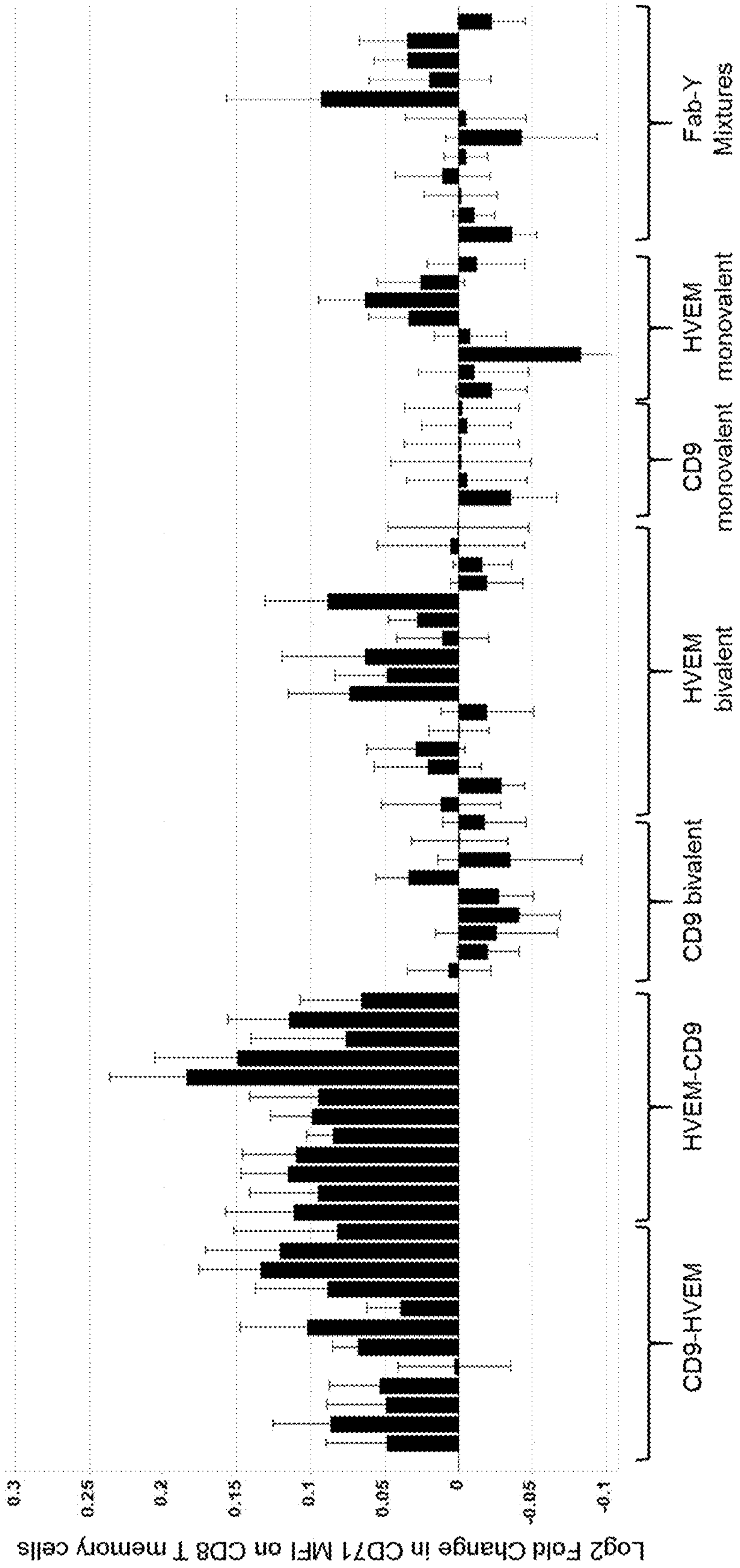
FIG. 12. Log 2 fold change in the MFI of CD71 expression on CD8+ T memory cells in the presence of SEB (1 μg/mL) stimulation. PBMC cultures were treated with *Staphylococcus Aureus* Enterotoxin B (SEB) at 1 μg/mL for 48 hours in the presence of either the HVEM-CD9 bispecific antibodies or control antibodies. The samples were then analysed by flow cytometry and the CD8+ memory T-cell population identified. Log 2 fold changes were calculated for the MFI of CD71 levels in the treated samples relative to the SEB stimulated controls. N=4 donors, 2 technical replicates ±SEM.
Figure 13:
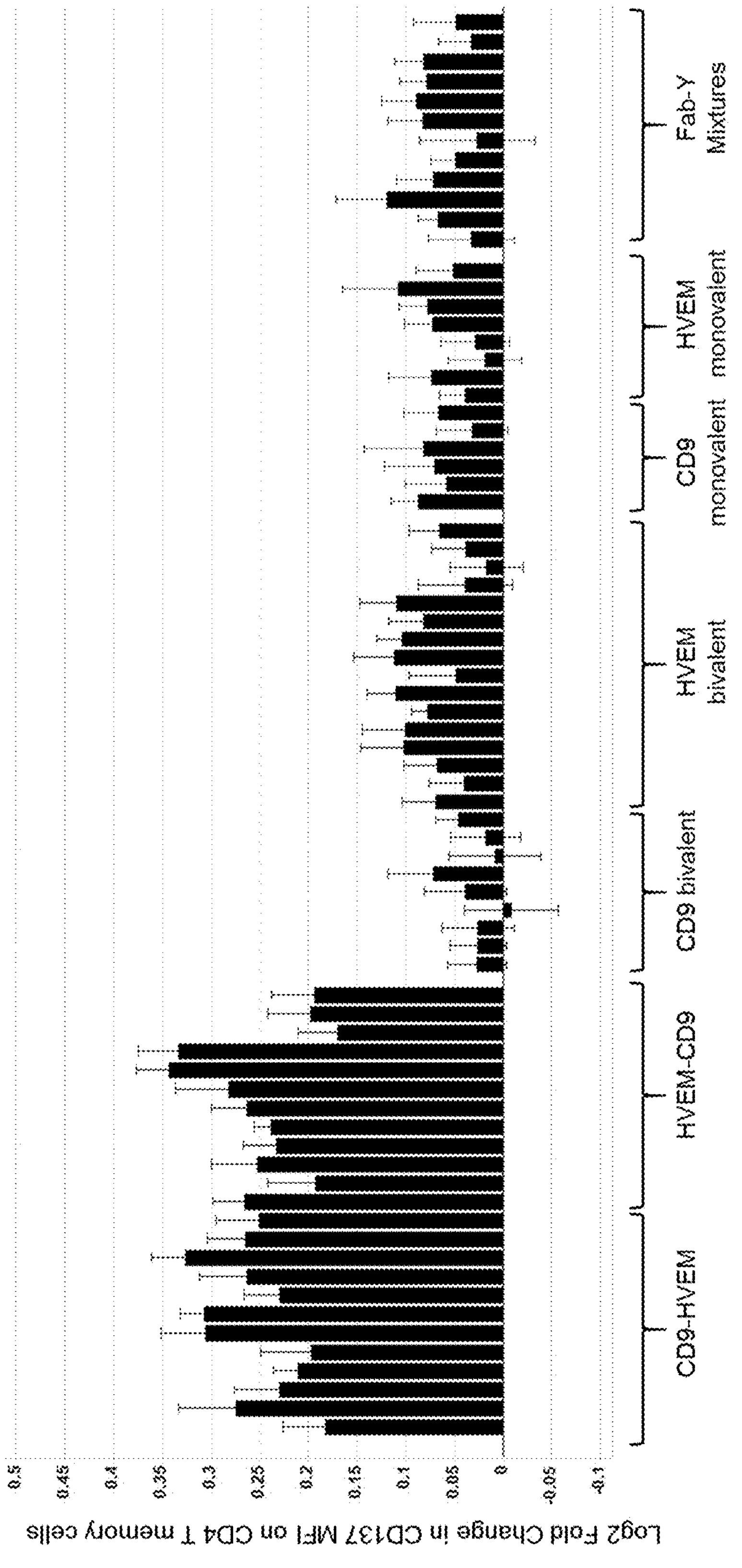
FIG. 13. Log 2 fold change in the MFI of CD137 expression on CD4+ T memory cells in the presence of SEB (lpg/mL) stimulation. PBMC cultures were treated with *Staphylococcus Aureus* Enterotoxin B (SEB) at 1 μg/mL for 48 hours in the presence of either the HVEM-CD9 bispecific antibodies or control antibodies. The samples were then analysed by flow cytometry and the CD4+ memory T-cell population identified. Log 2 fold changes were calculated for the MFI of CD137 levels in the treated samples relative to the SEB stimulated controls. N=4 donors, 2 technical replicates ±SEM.
Figure 14:
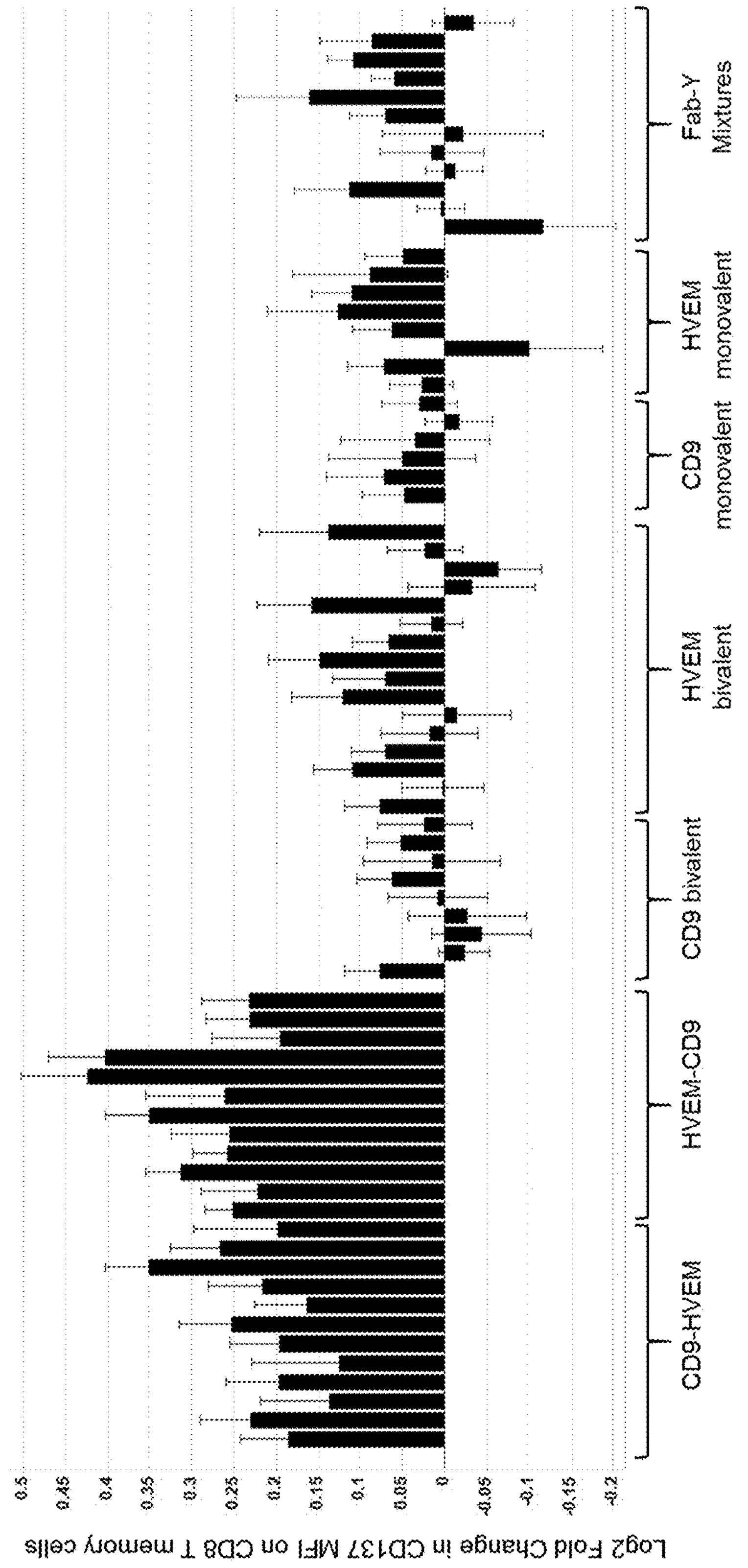
FIG. 14. Log 2 fold change in the MFI of CD137 expression on CD8+ T memory cells in the presence of SEB (1 μg/mL) stimulation. PBMC cultures were treated with *Staphylococcus Aureus* Enterotoxin B (SEB) at 1 μg/mL for 48 hours in the presence of either the HVEM-CD9 bispecific antibodies or control antibodies. The samples were then analysed by flow cytometry and the CD8+ memory T-cell population identified. Log 2 fold changes were calculated for the MFI of CD137 levels in the treated samples relative to the SEB stimulated controls. N=4 donors, 2 technical replicates ±SEM.

The levels of expression on CD4+ and CD8+ memory T-cells of CD71 (FIGS. 11 and 12, respectively) and CD137 (FIGS. 13 and 14, respectively) was also investigated. The HVEM/CD9 bispecific antibodies showed an effect resulting in increased levels of expression of CD71 and CD137 markers, irrespective of the orientation of the Fab-X/Fab-Y bispecific antibody.

The bivalents (i.e. formed by a fusion where both Fab in the Fab-X and Fab-Y are specific for CD9 or HVEM as the case may be) and monovalent antibodies for CD9 or HVEM (i.e. formed by a fusion where the Fab is specific for CD9 or HVEM but the other component Fab is a negative control) did not lead to a similar increase in the activation marker fluorescence intensity on either cell populations, suggesting that a monospecific antibody binding CD9 alone or HVEM alone, whether in a monovalent or bivalent fashion, is unable to stimulate activation in the absence of the binding to the other antigen.

Example 3: Effect of a HVEM-CD9 Bispecific Antibody on T-Cell Proliferation

The effect of an anti-HVEM-CD9 bispecific antibody on proliferation of CD4+ and CD8+ T-cells was assessed in 5 PBMC donors. Mixtures of fusion proteins Fab-X and Fab-Y were created by diluting equimolar (1 μM) quantities of Fab-X and Fab-Y with specificity for HVEM and CD9 in DMEM (Thermo Fisher) containing 10% foetal bovine serum (FBS) and 100 U/mL penicillin/100 μg/mL streptomycin. Mixtures of equimolar (1 μM) Fab-Y proteins were also generated in the same manner. The Fab-X and Fab-Y fusion proteins were incubated together for 1 hour (in a 37° C./5% $CO_2$ environment) to generate bispecific antibodies.

During this time, cryopreserved human PBMCs isolated from platelet leukapheresis cones were thawed, washed in DMEM media and resuspended at approximately $2\times10^6$ cells/mL in PBS. CellTrace™ Violet (CTV; ThermoFisher) was then added to a final concentration of 1 μM (2 μl 5 mM CTV in DMSO added to 10 mL cells), incubated in the dark at room temperature for 20 minutes, the cells washed twice with DMEM and resuspended in media to a final concentration of $1\times10^6$ cells/mL.

Fab-X/Fab-Y bispecific antibodies were diluted to 400 nM concentration in DMEM and 50 μl transferred in triplicate to wells of a 96 well U bottom tissue culture plate. Anti-CD3 (clone UCHT-1), 50 μl of a 200 ng/mL solution in DMEM, was then added. To 3 wells 100 μl DMEM media alone was added as a negative proliferation control. Finally, 100 μl of CTV labelled PBMC were added to each well. This resulted in a final assay concentration of Fab-X/Fab-Y bispecific antibodies of 100 nM, 50 ng/mL anti-CD3 and $1\times10^5$ cells/well. The plates were then returned to a 37° C./5% $CO_2$ environment for 96 hours.

After 96 hours the plates were centrifuged at 300×g for 5 minutes. Cell culture conditioned media was removed, the cells were washed twice with FACS buffer (2% FBS in PBS) and then resuspended in 50 μl FACS buffer containing fluorescently labelled antibodies, as listed in Table 3. The cells were incubated at room temperature in the dark for 20 minutes, washed twice with FACS buffer, resuspended in 100 μl/per well FACS buffer and analysed by flow cytometry (BD FACS Canto II™). Total events from 50 μl (50% volume) of each well were collected.

The data analysis software package FlowJo® was used to gate on CD8+ and CD4+ cells. Cell proliferation was assessed by enumerating cells with reduced CTV staining relative to unstimulated cells. The data are presented as the mean±SEM for triplicate wells.

TABLE 3

| Epitope | Fluorophore | Clone | Source | Dilution |
|---|---|---|---|---|
| CD8 | PE | RPA-T8 | BD | 100 |
| CD4 | APC | RPA-T4 | BioLegend ® | 20 |

Figure 15:
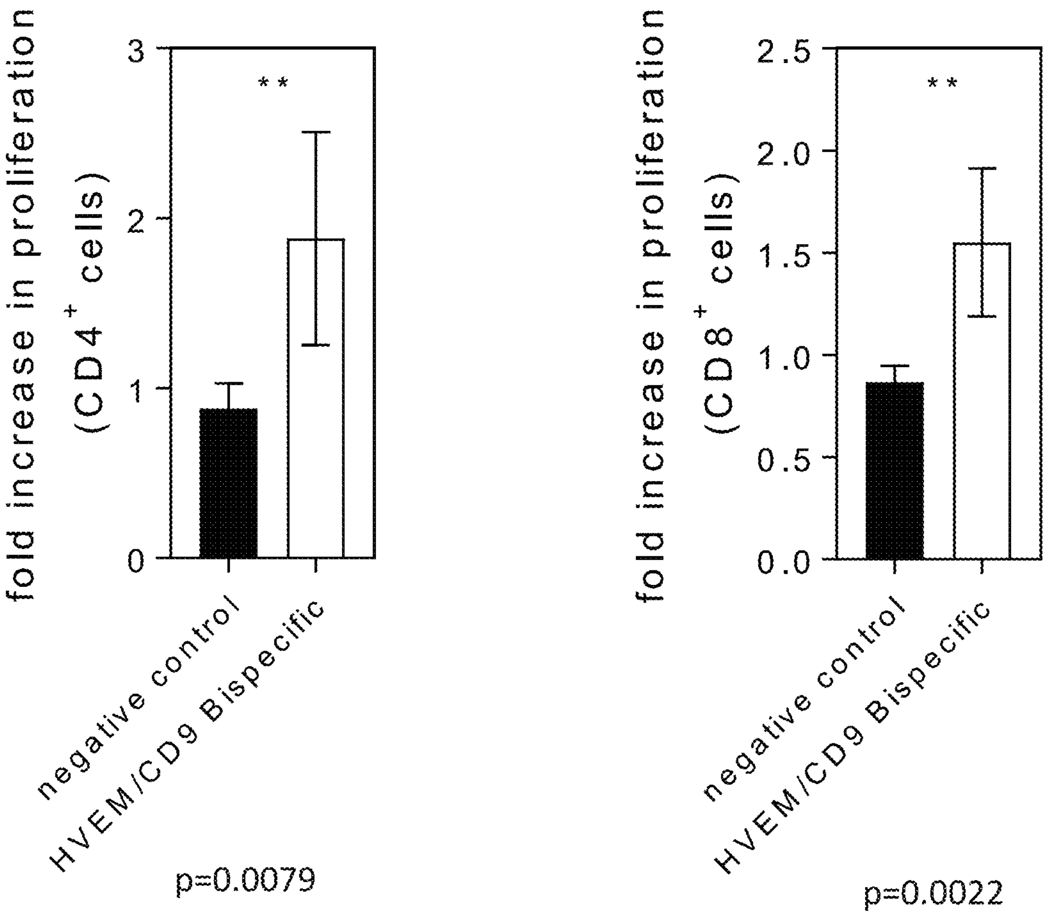
FIG. 15. Numbers of proliferating CD8+ and CD4+ T-cells in the presence of anti-CD3 (50 ng/mL; clone UCHT-1) stimulation. Human PBMC were labelled with CellTrace™ Violet (CTV) then incubated in triplicate for 4 days with anti-CD3 (clone UCHT-1) plus 100 nM of the HVEM-CD9 bispecific antibodies. T-cell proliferation was assessed by flow cytometry by gating on CD8+ and CD4+ populations and enumeration of CTV low cells. Results are presented as the mean±SEM of 5 PBMC donors and statistically significant differences with a p value <0.01 highlighted (Mann-Whitney test).
Figure 16:
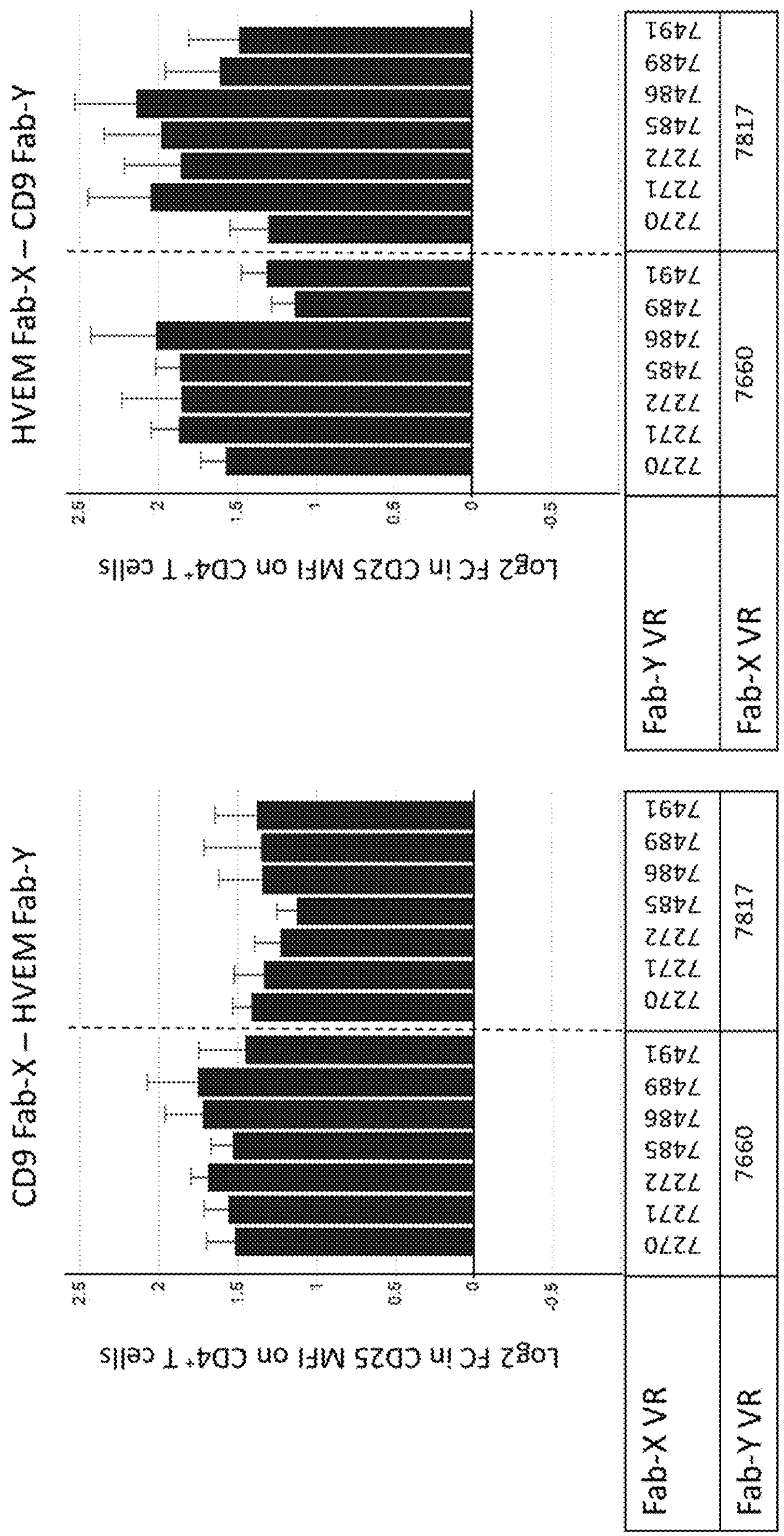
FIG. 16. $Log_2$ Fold Change in the MFI of CD25 expression on CD4+ T cells in the presence of SEB (1 μg/mL) stimulation. PBMC cultures were treated with *Staphylococcus aureus* Enterotoxin B (SEB) at 1 μg/mL for 48 hours in the presence of the HVEM-CD9 bispecific antibodies. The samples were then analysed by flow cytometry and the CD4+ T cell population identified. Log 2 fold changes were calculated for the MFI of CD25 levels in the treated samples relative to the SEB stimulated controls. N=2 donors, 2 technical replicates. ±SEM.

As shown in FIG. 15, proliferation of CD8+ and CD4+ T-cells in the presence of anti-CD3 (50 ng/mL) stimulation was statistically significantly higher when human PBMC were treated with the HVEM/CD9 bispecific antibody versus the negative control (no bispecific antibody) $p<0.01$ (Mann-Whitney test)

Example 4: Analysis of Anti-CD9 Antibody Binding by Biolayer Interferometry

CD9 contains two extracellular loops: a short extracellular loop (loop 1: 34-55 in SEQ ID NO:2) and a long extracellular loop (loop 2: 112-195 in SEQ ID NO:2). We used biolayer interferometry to assess binding of our panel of CD9 Fab-Y antibodies (selected for their ability to bind full-length cell-expressed CD9) to the long extracellular loop 2 peptide, using the Octet® RED384 System (ForteBio) with Anti-hlgG Fc Capture (AHC) Biosensors (ForteBio) at room temperature. Firstly, an array of 8 sensors was dipped in kinetics buffer (PBS 0.1%, BSA 0.02%, Tween 20) for 120 seconds to provide a baseline signal. Sensors were then moved to wells containing 200 μl of recombinant human CD9 long extracellular loop 2-human Fc fusion protein (10015-CD, R&D Systems®) at 2 μg/mL in kinetics buffer to immobilize the protein to the biosensor (100 seconds), followed by a second baseline step (180 seconds) in kinetics buffer to equilibrate the biosensors now coated with the CD9 long extracellular loop 2-human Fc fusion protein. No detachment of the peptide was observed during this step. Sensors were then dipped in wells containing one of the anti-CD9 Fab (10 μg/mL) to evaluate association of each antibody to CD9-loop2 (120 seconds), followed by dissociation in kinetics buffer (600 seconds). Anti-CD137 Fab-Y (11175) was used as negative control during the antibody association step. A new set of 8 biosensors was used to repeat this process for each of the anti-CD9 antibodies (7270, 7271, 7272, 7485, 7486, 7489, 7491).

As shown in Table 4, all the anti-CD9 antibodies tested bind to the long extracellular loop 2 of CD9 and all are functional when combined with anti-HVEM antibodies 7660 and 7817. A positive functional response is considered to be the capacity to increase CD25 expression on T cells greater than 0.5 log 2 fold change MFI in 2 donors when added as a Fab-$K_D$-Fab with anti-HVEM antibodies as shown in generated as in example 2 and shown in FIG. 17.

TABLE 4

| | CD9 long extracellular loop 2 | Functional (Y/N) |
|---|---|---|
| 7270 | ✓ | Y |
| 7271 | ✓ | Y |
| 7272 | ✓ | Y |
| 7485 | ✓ | Y |
| 7486 | ✓ | Y |
| 7489 | ✓ | Y |
| 7491 | ✓ | Y |

The invention claimed is:

1. An antibody which comprises a first antigen-binding portion binding HVEM and a second antigen-binding portion binding CD9, wherein the first antigen-binding portion binding HVEM comprises a first heavy chain variable region and a first light chain variable region, wherein the second antigen-binding portion binding CD9 comprises a second heavy chain variable region and a second light chain variable region, and wherein:

a. the first heavy chain variable region comprises a CDR-H1 comprising SEQ ID NO: 3, a CDR-H2 comprising SEQ ID NO: 4 and a CDR-H3 comprising SEQ ID NO: 5; and b. the first light chain variable region comprises a CDR-L1 comprising SEQ ID NO: 6, a CDR-L2 comprising SEQ ID NO: 7 and a CDR-L3 comprising SEQ ID NO: 8; and c. the second heavy chain variable region comprises a CDR-H1 comprising SEQ ID NO: 9, a CDR-H2 comprising SEQ ID NO: 10 and a CDR-H3 comprising SEQ ID NO: 11; and d. the second light chain variable region comprises a CDR-L1 comprising SEQ ID NO: 12, a CDR-L2 comprising SEQ ID NO: 13 and a CDR-L3 comprising SEQ ID NO: 14.

2. The antibody according to claim 1, wherein each of the antigen-binding portions is a monoclonal antigen-binding portion.

3. The antibody according to claim 1, wherein each of the antigen-binding portions is independently selected from a Fab, a Fab', or a scFv.

4. The antibody according to claim 1, wherein the antigen-binding portions are the antigen-binding portions of an IgG.

5. The antibody according to claim 1 wherein the antibody is chimeric, human or humanised.

6. The antibody according to claim 1, wherein the antibody comprises a heavy chain constant region selected from an IgG1, an IgG2, IgG3 or an IgG4 isotype, or a variant thereof.

7. The antibody according to claim 1, wherein the antibody further comprises at least an additional antigen-binding portion.

8. The antibody according to claim 7, wherein the additional antigen-binding portion is capable of increasing the half-life of the antibody.

9. The antibody according to claim 8, wherein the additional antigen-binding portion binds albumin.

10. The antibody according to claim 1, wherein the second antigen binding portion binds CD9 in CD9 loop 2.

11. The antibody according to claim 1, wherein:

the first heavy chain variable region comprises SEQ ID NO: 15 and the first light chain variable region comprises SEQ ID NO: 17; and the second heavy chain variable region comprises SEQ ID NO: 19 and second light chain variable region comprises SEQ ID NO: 21; or the first heavy chain variable region is encoded by a nucleotide sequence comprising SEQ ID NO: 16 and the first light chain variable region is encoded by a nucleotide sequence comprising SEQ ID NO: 18; and the second heavy chain variable region is encoded by a nucleotide sequence comprising SEQ ID NO: 20 and second light chain variable region is encoded by a nucleotide sequence comprising SEQ ID NO: 22.

12. A pharmaceutical composition comprising the antibody according to claim 1 and one or more pharmaceutically acceptable excipients.

* * * * *